(12) United States Patent
Thomas et al.

(10) Patent No.: US 7,365,225 B2
(45) Date of Patent: Apr. 29, 2008

(54) ARYL DICARBOXAMIDES

(75) Inventors: Russel J. Thomas, Siena (IT); Dominique Swinnen, Beaumont (FR); Jean-Francois Pons, Abingdon (GB); Agnes Bombrun, Monnetier-Mornex (FR)

(73) Assignee: Laboratoires Serono SA, Coinsins (CH)

( * ) Notice: Subject to any disclaimer, the term of this patent is extended or adjusted under 35 U.S.C. 154(b) by 0 days.

(21) Appl. No.: 10/565,557

(22) PCT Filed: Jul. 20, 2004

(86) PCT No.: PCT/EP2004/051558

§ 371 (c)(1),
(2), (4) Date: Jan. 23, 2006

(87) PCT Pub. No.: WO2005/011685

PCT Pub. Date: Feb. 10, 2005

(65) Prior Publication Data

US 2006/0189583 A1    Aug. 24, 2006

Related U.S. Application Data

(60) Provisional application No. 60/517,824, filed on Nov. 6, 2003.

(30) Foreign Application Priority Data

Jul. 21, 2003    (EP) .................................. 03102236

(51) Int. Cl.
    *C07C 53/134*    (2006.01)
    *C07C 63/04*    (2006.01)
    *A01N 43/78*    (2006.01)
    *A01N 37/10*    (2006.01)
    *C07D 277/20*    (2006.01)

(52) U.S. Cl. ...................... 562/496; 562/493; 514/365; 514/570; 514/568; 548/202

(58) Field of Classification Search ..................... None
See application file for complete search history.

(56) References Cited

FOREIGN PATENT DOCUMENTS

| WO | 00/69810 | 11/2000 |
|---|---|---|
| WO | 03/024955 | 3/2003 |
| WO | 03/064376 | 8/2003 |

OTHER PUBLICATIONS

Ganguly et al., Tetrahedron Letters (2002), 43, abstract.*
Watanabe et al., "Structure-Activity Relationship and Rational Design of 3,4-Dephostatin Derivatives as Protein Tyrosine Phosphatase Inhibitors", Tetrahedron, 56 (2000), 741-752.*
Swinnen et al. "Methylene amides, particularly [(arylmethyl)amino](oxo)acetic acids, useful as modulators, and especially inhibitors, of protein tyrosine phosphatases (PTPs), and their preparation, uses, e.g., as antidiabetics, and pharmaceutical compositions", CAPLUS AN 2003:610410, (abstract only).*
http://health.yahoo.com/topic/diabetes/overview/article/healthwise/hw34305.*
http://en.wikipedia.org/wiki/Hyperlipidemia.*
(http://www.healthscout.com/ency/68/366/ main.html.*
http://diabetes.webmd. com/guide/preventing-type-2-diabetes.*
http://www.webmd.com/diet/tc/Obesity-Overview.*
Asante Appiah et al., Am J Physiol. Endocrinol Metab, 2003, 284, E663-E670.*
Elchebly et al., Science 283, 1544 (1999); p. 1544-1548.*
http://www.centerwatch.com/patient/nmtresults/nmt030929.html.*
Choong, Ingrid C. et al., "Identification of Potent and Selective Small-Molecule Inhibitors of Caspase-3 through the Use of Extended Tethering and Structure-Based Drug Design", Journal of Medicinal Chemistry, vol. 45, No. 23, pp. 5005-5022, 2002.
Ahima, Rexford S. et al., "Leptin", Annu. Rev. Physiol., vol. 62, pp. 413-437, 2000.

(Continued)

*Primary Examiner*—Kamal A. Safed
*Assistant Examiner*—Sun Jae Y Loewe
(74) *Attorney, Agent, or Firm*—Oblon, Spivak, McClelland, Maier & Neustadt, P.C.

(57) ABSTRACT

The present invention is related to aryl dicarboxamides of formula (I) and use thereof for the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). In particular, the present invention is related to the use of aryl dicarboxamides of formula (I) to modulate, notably to inhibit the activity of PTPs. A is an aminocarbonyl moiety; Cy is an aryl, heteroaryl, aryl-heteroaryl, heteroaryl-aryl, aryl-aryl, cycloalkyl or heterocycle group; n is either 0 or 1; $R^1$ and $R^2$ are independently from each other is selected from the group consisting of hydrogen or $C_1$-$C_6$-alkyl; $R^4$ and $R^5$ are each independently from each other selected from the group consisting of H, hydroxy, $C_1$-$C_6$ alkyl, carboxy, $C_1$-$C_6$ alkoxy, $C_1$-$C_3$ alkyl carboxy, $C_2$-$C_3$ alkenyl carboxy, $C_2$-$C_3$ alkynyl carboxy, amino or $R^4$ and $R^5$ may form an unsaturated or saturated heterocyclic ring, whereby at least one of $R^4$ or $R^5$ is not a hydrogen or $C_1$-$C_6$ alkyl

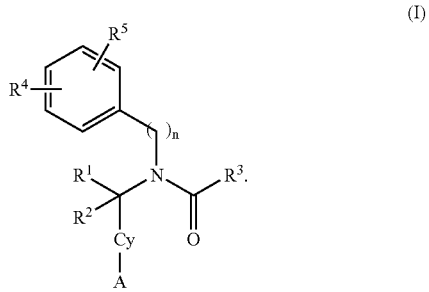

8 Claims, No Drawings

OTHER PUBLICATIONS

Bergnes, Gustave et al., "Generation of an Ugi Library of phosphate mimic-containing compounds and identification of novel dual specific phosphatase inhibitors", Bioorganic & Medicinal Chemistry Letters, vol. 9, pp. 2849-2854, 1999.

Bjorge, Jeffrey D. et al., "Identification of protein-tyrosine phosphatase 1B as the major tyrosine phosphatase activity Capable of dephosphorylating and activating c-src in several human breast cancer cell lines", The Journal of Biological Chemistry, vol. 275, No. 52, pp. 41439-41446, 2000.

Cheng, Alan et al., "Attenuation of leptin action and regulation of obesity by protein tyrosine phosphatase 1B", Developmental cell, vol. 2, pp. 497-503, 2002.

Defronzo, Ralph A. et al., "Insulin Resistance: A Multifaceted syndrome responsible for NIDDM, Obesity, Hypertension, Dyslipidemia, and atherosclerotic cardiovascular disease", Diabetes Care, vol. 14, No. 3, pp. 173-194, 1991.

Diamanti-Kandarakis, Evanthia et al., "Therapeutic effects of metformin on insulin resistance and hyperandrogenism in polycystic ovary syndrome", European Journal of Endocrinology, vol. 138, pp. 269-274, 1998.

Dunaif, "Insulin resistance and the polycystic ovary syndrome: mechanism and implications for pathogenesis", Endocrine Reviews, vol. 18, No. 6, pp. 774-800, 1997.

Elchebly, Mounib et al., "Modulation of insulin signaling by protein tyrosine phosphatases", J. Mol. Med., vol. 78, pp. 473-482, 2000.

Jarrett, R. J., "Cardiovascular disease and hypertension in diabetes mellitus", Diabetes/Metabolism Reviews, vol. 5, No. 7, pp. 547-558, 1989.

Kennedy, Brian P. et al., "Protein tyrosine phosphatase- 1b in diabetes", Biochemical Pharmacology, vol. 60, pp. 877-883, 2000.

Klaman, Lori D. et al., "Increased energy expenditure, decreased adiposity, and tissue-specific insulin sensitivity in protein-tyrosine phosphatase 1B-deficient mice", Molecular and Cellular Biology, vol. 20, No. 15, pp. 5479-5489, 2000.

McGuire, Mary C. et al., "Abnormal regulation of protein tyrosine phosphatase activities in skeletal muscle of insulin-resistant humans", Diabetes, vol. 40, pp. 939-942, 1991.

Meyerovitch, Joseph, et al., "Hepatic phosphotyrosine phosphatase activity and its alterations in diabetic rats", J. Clinical Invest, vol. 84, pp. 976-983, 1989.

Moller, et al., "Protein tyrosine phosphatases (PTPs) as drug targets: Inhibitors of PTP-1B for the treatment of diabetes", Current Opinion in Drug Discovery & Development, vol. 3, No. 5, pp. 527-540, 2000.

Pathre, Purnima et al., "PTP1B regulates neurite extension mediated by cell-cell and cell-matrix adhesion molecules", Journal of Neuroscience Research, vol. 63, No. 2, pp. 143-150, 2001.

Reaven, Gerald M. et al., "Nonketotic diabetes mellitus: insulin deficiency or insulin resistance?", The American Journal of Medicine, vol. 60, pp. 80-88, 1976.

Shock, Lisa P. et al., "Protein tyrosine phosphatases expressed in developing brain and retinal Mueller glia", Molecular Brain Research, vol. 28, No. 1, pp. 110-116, 1995.

Sredy, Janet et al., "Insulin resistance is associated with abnormal dephosphorylation of a synthetic phosphopeptide corresponding to the major autophosphorylation sites of the insulin receptor", Metabolism, vol. 44, No. 8, pp. 1074-1081, 1995.

Stout, Robert W., "Overview of the association between insulin and atherosclerosis", Metabolism, vol. 34, No. 12, pp. 7-12, 1985.

Zhang, Zhong-Yin, "Protein tyrosine phosphatases: prospects for therapeutics", Curr. Opin., Chem, Biol., vol. 5, No. 4, pp. 416-423, 2001.

* cited by examiner

ARYL DICARBOXAMIDES

FIELD OF THE INVENTION

The present invention is related to aryl dicarboxamides of formula (I), in particular for the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). The compounds of this invention are particularly useful in the treatment of type II diabetes, obesity or the regulation of appetite. Specifically, the present invention is related to aryl dicarboxamides for the modulation, notably the inhibition of the activity of PTPs, in particular of PTP1B.

BACKGROUND OF THE INVENTION

The prevalence of insulin resistance in glucose intolerant subjects is well known. Reaven et al (*American Journal of Medicine*, 60, 80 (1976)) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyperinsulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity and with ischemic diseases of the large blood vessels (e.g. atherosclerosis) has been well established by numerous experimental, clinical and epidemiological studies (Stout, *Metabolism*, 34, 7 (1985)). Statistically significant plasma insulin elevations at 1 and 2 hours after oral glucose load correlate with an increased risk of coronary heart disease.

Since most of these studies actually excluded diabetic subjects, data relating the risk of atherosclerotic diseases to the diabetic condition are not as numerous, but point in the same direction as for non-diabetic subjects. However, the incidence of atherosclerotic diseases in morbidity and mortality statistics in the diabetic population exceeds that of the nondiabetic population (Jarrett *Diabetes/Metabolism Reviews*, 5, 547 (1989)).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* 138, 269-274 (1998), Andrea Dunaif; Insulin Resistance and the Polycystic Ovary Syndrome: Mechanism and Implications for Pathogenesis; *Endocrine Reviews* 18(6), 774-800 (1997)).

The independent risk factors obesity and hypertension for atherosclerotic diseases are also associated with insulin resistance. Using a combination of insulin/glucose clamps, tracer glucose infusion and indirect calorimetry, it was demonstrated that the insulin resistance of essential hypertension is located in peripheral tissues (principally muscle) and correlates directly with the severity of hypertension (DeFronzo and Ferrannini, *Diabetes Care*, 14, 173 (1991)).

In hypertension of obese people, insulin resistance generates hyperinsulinemia, which is recruited as a mechanism to limit further weight gain via thermogenesis, but insulin also increases renal sodium re-absorption and stimulates the sympathetic nervous system in kidneys, heart, and vasculature, creating hypertension.

It is assumed that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Mounib Elchebly, Alan Cheng, Michel L. Tremblay; Modulation of insulin signaling by protein tyrosine phosphatases; *J. Mol. Med.* 78, 473-482 (2000)).

Protein-tyrosine phosphatases (PTPs) play an important role in the regulation of phosphorylation of proteins and represent the counterparts of kinases. Among classical PTPs, there are two types: (i) non-receptor or intracellular PTPs and (ii) receptor-like PTPs. Most intracellular PTPs contain one catalytic domain only, whereas most receptor-like enzymes contain two. The catalytic domain consists of about 250 amino acids (Niels Peter Hundahl Moller et al. Protein tyrosine phosphatases (PTPs) as drug targets: Inhibitors of PTP-1B for the treatment of diabetes; *Current Opinion in Drug Discovery & Development* 3(5), 527-540 (2000)).

The interaction of insulin with its receptor leads to phosphorylation of certain tyrosine molecules within the receptor protein, thus activating the receptor kinase. PTPs dephosphorylate the activated insulin receptor, attenuating the tyrosine kinase activity. PTPs can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTP-alpha and SH-PTP2 (Lori Klaman et al.; Increased Energy Expenditure, Decreased Adiposity, and Tissue-specific insulin sensitivity in Protein-Tyrosine Phosphatase 1B-Deficient Mice; *Molecular and Cellular Biology*, 5479-5489 (2000)).

PTP1B is a member of the PTP family. This 50 kDa protein contains a conserved phosphatase domain at residues 30-278 and is localized to the cytoplasmic ice of the endoplasmic reticulum by its C-terminal 35 residues. Its interactions with other proteins are mediated by proline-rich regions and SH2 compatible sequence. PTP1B is believed to act as a negative regulator in insulin signaling.

McGuire et al. (*Diabetes*, 40, 939 (1991)) demonstrated that non-diabetic glucose intolerant subjects possessed significantly elevated levels of PTP activity in muscle tissue vs. normal subjects, and that insulin infusion failed to suppress PTP activity as it did in insulin sensitive subjects.

Meyerovitch et al. (*J. Clinical Invest.*, 84, 976 (1989)) observed significantly increased PTP activity in the livers of two rodent models of IDDM, the genetically diabetic BB rat, and the STZ-induced diabetic rat. Sredy et al. (*Metabolism*, 44, 1074, (1995)) observed similar increased PTP activity in the livers of obese, diabetic ob/ob mice, which represent a typical rodent model of NIDDM.

Zhang et al (*Curr. Opin. Chem. Biol.*, 5(4), 416-23 (2001)) found that PTPs are also implicated in a wide variety of other disorders, including cancer. Bjorge, J. D. et al. (*J. Biol. Chem.*, 275(52), 41439-46 (2000)) indicates that PTP1B is the primary protein-tyrosine phosphatase capable of dephosphorylating c-Src in several human breast cancer cell lines and suggests a regulatory role for PTP1B in the control of c-Src kinase activity.

Pathre et al (*J. Neurosci. Res.*, 63(2), 143-150 (2001)) describes that PTP1B regulates neurite extension mediated by cell-cell and cell-matrix adhesion molecules. Further, Shock L. P et al. (*Mol. Brain. Res.*, 28(1), 110-16 (1995)) demonstrates that a distinct overlapping set of PTPs is expressed in the developing brain and retinal Mueller glia, including 2 novel PTPs that may participate in neural cell communication.

The insulin receptor (IR) is a prototypical tyrosine kinase receptor whose ligand binding and dimerization results in auto-phosphorylation on multiple tyrosines. This is followed by the recruitment and phosphorylation of IRS1-4 (depending on the tissue) and PI3K. Although vanadium-containing compounds have been known since the 19$^{th}$ century to alleviate diabetes, it was understood only recently that these inhibitors stimulate the insulin signaling pathway by blocking PTP action. Evidence for the involvement of the IR (insulin receptor) and IRS-1 in this phenotype was that both proteins show increased tyrosine phosphorylation in the PTP1B-mutated mice. The available data strongly suggest that in particular PTP1B is a promising target for the development of drugs to treat diabetes and obesity (Brian P. Kennedy and Chidambaram Ramachandran; Protein Tyrosine Phosphatase-1B in Diabetes; *Biochemical Pharmacology*, Vol. 60, 877-883, (2000)).

A further protein involved in obesity is Leptin. Leptin is a peptide hormone that plays a central role in feeding and adiposity (Leptin, *Annu. Rev. Physiol.* 62 p. 413-437 (2000) by Ahima R. S. et al.). Recently, it has been suggested that PTP1B negatively regulates leptin signaling, and provides one mechanism by which it may regulate obesity. Further, it is known that pharmacological inhibitors of PTP1B hold promise as an alternative or a supplement to leptin in the treatment of obesity due to leptin resistance (*Developmental Cell.*, vol. 2, p. 497-503 (2002)).

In numerous patent application small molecules have been proposed as inhibitors of PTPs.

Substituted aryl and heteroaryl derivatives of benzamidines are described by G. Bergnes et al., in *Bioorganic Medicinal Chemistry Letters* 9(19) p. 2849-5, (1999).

WO 03/024955 discloses the following compound which does not fall under formula (I):

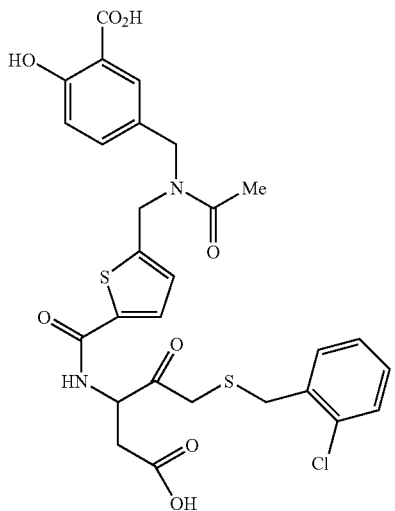

SUMMARY OF THE INVENTION

The present invention relates to aryl dicarboxamides of formula (I).

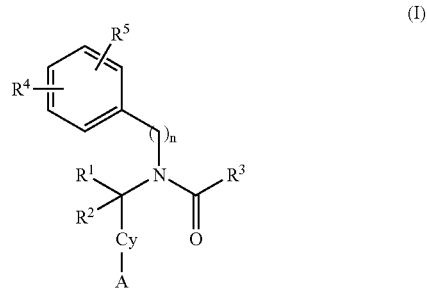

Such compounds are suitable for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). The compounds of this invention are inhibitors of PTPs.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"PTPs" are protein tyrosine phosphatases and include for instance PTP1B, TC-PTP, PTP-β, PTP-H1, DEP-1, LAR, SHP-1, SHP-2, GLEPP-1, PT-μ, VHR, hVH5, LMW-PTP, PTEN.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH═CH$_2$), n-2-propenyl (allyl, —CH$_2$CH═CH$_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g. norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N⁺RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl", optionally substituted with halogens, e.g a —S—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfinyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR'[0 where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-specified compounds of formula (I). Examples of such salts include, but are not restricted, to base addition salts formed by reaction of compounds of formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, choline, L-lysine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. Such masking group may be an ester moiety.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereoisomers and its racemate forms, as well as pharmaceutically acceptable salts thereof. Preferred pharmaceutically acceptable salts of the formula (I), are base addition salts formed by reaction of compounds of formula (I) with pharmaceutically acceptable bases like N-methyl-D-glucamine, tromethamine, sodium, potassium or calcium salts of carbonates, bicarbonates or hydroxides.

The aryl dicarboxamides according to the present invention are those of formula (I):

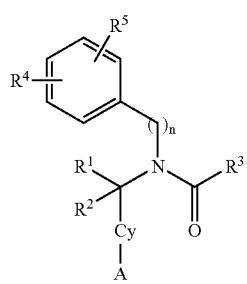

(I)

Formula (I) comprises also the geometrical isomers, the optically active forms, including enantiomers, diastereomers and its racemate forms, as well as pharmaceutically acceptable salts and pharmaceutically active derivatives thereof.

The substituents $R^1$, $R^2$, $R^3$, $R^4$, $R^5$, n and Cy within Formula (I) are defined as follows:

A is an aminocarbonyl moiety of the formula —CO—NHR$^6$ wherein $R^6$ is $C_6$-$C_{15}$ alkyl, $C_2$-$C_{15}$-alkenyl, $C_2$-$C_{15}$-alkynyl, a 3-8 membered cycloalkyl, $C_1$-$C_6$ alkyl-(3-8 membered) cycloalkyl, phenyl, $C_1$-$C_{12}$ alkyl phenyl, $C_2$-$C_6$-alkenyl phenyl, $C_2$-$C_6$-alkynyl phenyl.

n is either 0 or 1.

Cy is a substituted or unsubstituted aryl, substituted or unsubstituted heteroaryl, substituted or unsubstituted aryl-heteroaryl, substituted or unsubstituted heteroaryl-aryl, substituted or unsubstituted aryl-aryl, substituted or unsubstituted cycloalkyl or substituted or unsubstituted heterocycle group.

Such aryl or heteroaryl include phenyl, naphthyl, phenantrenyl, pyrrolyl, furyl, thienyl, imidazolyl, pyridyl, oxazolyl, isoxazolyl, thiazolyl, isothiazolyl, pyrazolyl, 1,2,3-triazolyl, 1,2,4-triazolyl, 1,2,3-oxadiazolyl, benzo(1,2,5)oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzopyrimidinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, benzothiazolyl, benzoxazolyl, pyridazinyl, pyrimidyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl 5,6,7,8-tetrahydroisoquinolyl, purinyl, pteridinyl, xanthenyl, benzoquinolyl, oxolanyl, pyrolidinyl, pyrazolidinyl, 2H-benzo[d]1,3-dioxolenyl, indanyl, imidazolidinyl, 1,2,4-oxadiazolidinyl, 1,2,5-oxadiazolidinyl, 1,3,4-oxadiazolidinyl or isoxazolidinyl.

According to one embodiment Cy is a substituted or unsubstituted phenyl, substituted or unsubstituted thiazolyl, substituted or unsubstituted phenyl-thiazolyl, substituted or unsubstituted thiazolyl-phenyl.

$R^1$ and $R^2$ are independently from each other is selected from the group consisting of hydrogen or substituted or unsubstituted ($C_1$-$C_6$)alkyl. According to one embodiment both $R^1$ and $R^2$ are hydrogen.

$R^3$ is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted $C_1$-$C_6$-alkoxy, substituted or unsubstituted $C_1$-$C_6$-alkyl amine, substituted or unsubstituted $C_1$-$C_6$-alkyl alkoxy, substituted or unsubstituted aryl, substituted or unsubstituted heteroaryl, substituted or unsubstituted saturated or unsaturated 3-8-membered cycloalkyl, substituted or unsubstituted 3-8-membered heterocycloalkyl, substituted or unsubstituted $C_1$-$C_6$-alkyl aryl, substituted or unsubstituted $C_1$-$C_6$-alkyl heteroaryl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, substituted or unsubstituted $C_2$-$C_6$-alkynyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl cycloalkyl, substituted or unsubstituted $C_2$-$C_6$-alkenyl heterocycloalkyl, substituted or unsubstituted $C_2$-$C_6$-alynyl cycloalkyl, substituted or unsubstituted $C_2$-$C_6$-alkynyl heterocycloalkyl.

$R^4$ and $R^5$ are each independently from each other selected from the group consisting of H, hydroxy, substituted or unsubstituted $C_1$-$C_6$ alkyl, carboxy, substituted or unsubstituted $C_1$-$C_6$ alkoxy, substituted or unsubstituted $C_1$-$C_3$ alkyl carboxy, substituted or unsubstituted $C_2$-$C_3$ alkenyl carboxy, substituted or unsubstituted $C_2$-$C_3$ alkynyl carboxy, amino.

Alternatively, $R^4$ and $R^5$ may form an unsaturated or saturated substituted or unsubstituted heterocyclic ring, e.g. a 2,2-dimethyl-4-oxo-4H-1,3-benzodioxin-4-one.

At any rate, at least one of $R^4$ or $R^5$ is not a hydrogen or $C_1$-$C_6$ alkyl.

In one specific embodiment $R^6$ is selected from the group consisting of $C_8$-$C_{12}$ alkyl, $C_1$-$C_4$ alkyl phenyl which may be substituted by $C_1$-$C_8$ alkyl or phenoxy.

More specific aryl dicarboxamides of the present invention have of the formulae (Ia), (Ib) or (Ic):

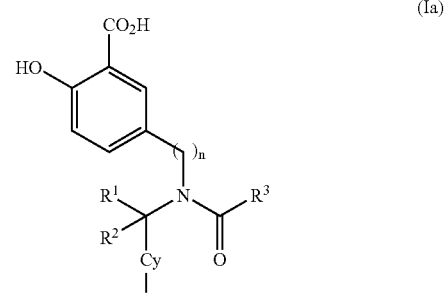

(Ia)

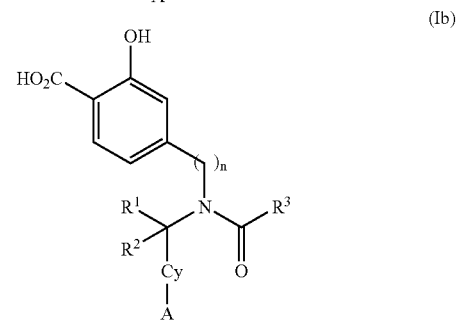

(Ib)

-continued

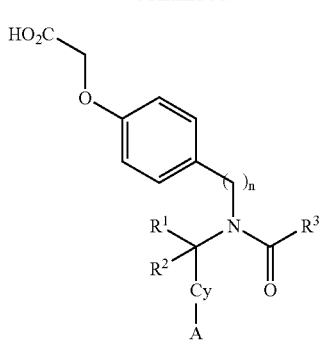

(Ic)

wherein A, Cy, n, R¹, R² and R³ are as above defined.

Specific aryl dicarboxamide according to formula (I) comprise the following:

5-[(3-cyclopentylpropanoyl)(4-{[(4-phenoxybenzyl)amino]carbonyl}benzyl)amino]-2-hydroxybenzoic acid 5-[(3-cyclopentylpropanoyl)(4-{[(4-phenoxybenzyl)amino]carbonyl}benzyl)amino]-2-hydroxybenzoic acid

[4-({{[2-(4-{[(4-pentylbenzyl)amino]carbonyl}phenyl)-1,3-thiazol-4-yl]methyl}[(2E)-2-phenylprop-2-enoyl]amino}methyl)phenoxy]acetic acid 5-[(3-cyclopentylpropanoyl)(4-{[(4-pentylbenzyl)amino]carbonyl}benzyl)amino]-2-hydroxybenzoic acid 2-hydroxy-5-{(4-{[(4-pentylbenzyl)amino]carbonyl}benzyl)[4-(trifluoromethyl)benzoyl]amino}benzoic acid 2-hydroxy-5-[[(4-{[(4-phenoxybenzyl)amino]carbonyl}-1,3-thiazol-2-yl)methyl](3-phenylpropanoyl)amino]benzoic acid 5-{benzoyl[(4-f{[(4-phenoxybenzyl)amino]carbonyl}-1,3-thiazol-2-yl)methyl]amino}-2-hydroxybenzoic acid 2-hydroxy-5-{[(4-{[(4-phenoxybenzyl)amino]carbonyl}-1,3-thiazol-2-yl)methyl][4-(trifluoromethyl)benzoyl]amino}benzoic acid 5-[(cyclohexylcarbonyl)(4-{[(4-phenoxybenzyl)amino]carbonyl}benzyl)amino]-2-hydroxybenzoic acid 2-hydroxy-5-[(4-{[(4-phenoxybenzyl)amino]carbonyl}benzyl)(3-phenylpropanoyl)amino]benzoic acid 5-[benzoyl(4-{[(4-phenoxybenzyl)amino]carbonyl}benzyl)amino]-2-hydroxybenzoic acid 5-[acetyl(4-{[(4-phenoxybenzyl)amino]carbonyl}benzyl)amino]-2-hydroxybenzoic acid 5-[(4-cyanobenzoyl)(4-f{[(4-phenoxybenzyl)amino]carbonyl}benzyl)amino]-2-hydroxybenzoic acid 2-hydroxy-5-[(phenoxyacetyl)(4-{[(4-phenoxybenzyl)amino]carbonyl}benzyl)amino]-benzoic acid 2-hydroxy-5-{(4-{[(4-phenoxybenzyl)amino]carbonyl}benzyl)[4-(trifluoromethyl)benzoyl]amino}benzoic acid 2-hydroxy-5-{(4-{[(4-phenoxybenzyl)amino]carbonyl}benzyl)[(2E)-3-phenylprop-2-enoyl]amino}benzoic acid 5-[(N,N-dimethylglycyl)(4-{[(4-phenoxybenzyl)amino]carbonyl}benzyl)amino]-2-hydroxybenzoic acid 2-hydroxy-5-[(3-methylbut-2-enoyl)(4-{[(4-phenoxybenzyl)amino]carbonyl}benzyl)amino]benzoic acid 2-hydroxy-5-{[{4-[(octylamino)carbonyl]benzyl}(phenoxyacetyl)amino]methyl}benzoic acid 2-hydroxy-5-({{4-[(octylamino)carbonyl]benzyl}[4-(trifluoromethyl)benzoyl]amino}-methyl)benzoic acid 2-hydroxy-5-({{4-[(octylamino)carbonyl]benzyl}[(2E)-3-phenylprop-2-enoyl]amino}methyl)benzoic acid 5-{[(3-cyclopentylpropanoyl)({[(4-pentylbenzyl)amino]carbonyl}benzyl)amino]methyl}-2-hydroxybenzoic acid 2-hydroxy-5-{[(4-{[(4-pentylbenzyl)amino]carbonyl}benzyl)(phenoxyacetyl)amino]-methyl}benzoic acid 2-hydroxy-5-({(4-{[(4-pentylbenzyl)amino]carbonyl}benzyl)[4-(trifluoromethyl)benzoyl]-amino}methyl)benzoic acid 2-hydroxy-5-{[(3-methylbut-2-enoyl)(4-{[(4-pentylbenzyl)amino]carbonyl}benzyl)amino]-methyl}benzoic acid 5-{[(3-cyclopentylpropanoyl)(4-{[(4-phenylbutyl)amino]carbonyl}benzyl)amino]methyl}-2-hydroxybenzoic acid 2-hydroxy-5-({[(4-{[(4-pentylbenzyl)amino]carbonyl}-1,3-thiazol-2-yl)methyl][(2-phenylprop-2-enoyl]amino}methyl)benzoic acid

[4-({(4-{[(4-phenoxybenzyl)amino]carbonyl}benzyl)[4-(trifluoromethyl)benzoyl]amino}-methyl)phenoxy]acetic acid 2-hydroxy-5-[(4-{[(4-pentylbenzyl)amino]carbonyl}benzyl)(3-phenylpropanoyl)amino]-benzoic acid 4-[(3-cyclopentylpropanoyl)(4-{[(4-pentylbenzyl)amino]carbonyl}benzyl)amino]-2-hydroxybenzoic acid 2-hydroxy-4-{(4-{[(4-pentylbenzyl)amino]carbonyl}benzyl)[4-(trifluoromethyl)benzoyl]amino}benzoic acid 2-hydroxy-5-[{[2-(4-{[(4-pentylbenzyl)amino]carbonyl}phenyl)-1,3-thiazol-4-yl]methyl}(phenoxyacetyl)amino]benzoic acid 2-hydroxy-5-{{[2-(4-{[(4-pentylbenzyl)amino]carbonyl}phenyl)-1,3-thiazol-4-yl]methyl}[4-(trifluoromethyl)benzoyl]amino}benzoic acid 5-([[(6-chloropyridin-3-yl)carbonyl]{[2-(4-{[(4-pentylbenzyl)amino]carbonyl}phenyl)-1,3-thiazol-4-yl]methyl}amino)-2-hydroxybenzoic acid 5-((4-cyanobenzoyl){[2-(4-{[(4-pentylbenzyl)amino]carbonyl}phenyl)-1,3-thiazol-4-yl]methyl[56 amino)-2-hydroxybenzoic acid 2-hydroxy-5-((3-methylbut-2-enoyl){[2-(4-{[(4-pentylbenzyl)amino]carbonyl}phenyl)-1,3-thiazol-4-yl]methyl}amino)benzoic acid 5-((3-cyclopentylpropanoyl){[2-(4-{[(4-phenoxybenzyl)amino]carbonyl}phenyl)-1,3-thiazol-4-yl]methyl}amino)-2-hydroxybenzoic acid 2-hydroxy-5-{{[2-(4-{[(4-phenoxybenzyl)amino]carbonyl}phenyl)-1,3-thiazol-4-yl]methyl}[4-(trifluoromethyl)benzoyl]amino}benzoic acid 2-hydroxy-5-[{[2-(4-{[(4-phenoxybenzyl)amino]carbonyl}phenyl)-1,3-thiazol-4-yl]methyl}(3-phenylpropanoyl)amino]benzoic acid 5-(benzoyl{[2-(4-[55 [(4-phenoxybenzyl)amino]carbonyl}phenyl)-1,3-thiazol-4-yl]methyl}amino)-2-hydroxybenzoic acid

[4-({{[2-(4-{[(4-pentylbenzyl)amino]carbonyl}phenyl)-1,3-thiazol-4-yl]methyl}[4-(trifluoromethyl)benzoyl]amino}methyl)phenoxy]acetic acid (4-{[{[2-(4-{[(4-pentylbenzyl)amino]carbonyl}phenyl)-1,3-thiazol-4-yl]methyl}(3-phenylpropanoyl)amino]methyl}phenoxy)acetic acid

[4-({{[2-(4-{[(4-phenylbutyl)amino]carbonyl}phenyl)-1,3-thiazol-4-yl]methyl}[4-(trifluoromethyl)benzoyl]amino}methyl)phenoxy]acetic acid (4-{[{[2-(4-{[(4-phenylbutyl)amino]carbonyl}phenyl)-1,3-thiazol-4-yl]methyl}(3-phenylpropanoyl)amino]methyl}phenoxy)acetic acid

[4-({{[2-(4-{[(4-phenylbutyl)amino]carbonyl}phenyl)-1,3-thiazol-4-yl]methyl}[(2E)-3-phenylprop-2-enoyl]amino}methyl)phenoxy]acetic acid {4-[((N,N-dimethylglycyl){[2-(4-{[(4-phenylbutyl)amino]carbonyl}phenyl)-1,3-thiazol-4-yl]methyl}amino)methyl]phenoxy}acetic acid {4-[((cyclohexylcarbonyl){[2-(4-{[(4-phenylbutyl)amino]carbonyl}phenyl)-1,3-thiazol-4-yl]methyl}amino)methyl]phenoxy}acetic acid {4-[(phenoxyacetyl){[2-(4-{[(4-phenoxybenzyl)amino]carbonyl}phenyl)-1,3-thiazol-4-yl]methyl}amino)methyl]phenoxy}acetic acid

[4-({{[2-(4-{[(4-phenoxybenzyl)amino]carbonyl}phenyl)-1,3-thiazol-4-yl]methyl}[4-(trifluoromethyl)benzoyl]amino}methyl)phenoxy]acetic acid (4-{[{[2-(4-{[(4-phenoxybenzyl)amino]carbonyl}phenyl)-1,3-thiazol-4-yl]methyl}(3-phenylpropanoyl)amino]methyl}phenoxy)acetic acid {4-[((cyclohexylcarbonyl){[2-(4-{[(4-phenoxybenzyl)amino]carbonyl}phenyl)-1,3-thiazol-4-yl[methyl}amino)methyl[phenoxy}acetic acid

[4-({[(2-{4-[(octylamino)carbonyl]phenyl}-1,3-thiazol-4-yl)methyl][4-(trifluoromethyl)-benzoy[amino}methyl)phenoxy]acetic acid (4-{[[(2-{4-[(octylamino)carbonyl]phenyl}-1,3-thiazol-4-yl)methyl](3-phenylpropanoyl)-amino[methyl}phenoxy)acetic acid The compounds of formula (I) are useful in the treatment and/or prevention of obesity and/or metabolic disorders mediated by insulin resistance or hyperglycemia, comprising diabetes type I and/or II, inadequate glucose tolerance, insulin resistance, hyperlipidemia, hypertri-glyceridemia, hypercholesterolemia or polycystic ovary syndrome (PCOS).

In one embodiment the compounds according to formula (I) are particularly useful in the treatment and/or prevention of diabetes type II, obesity and for the regulation of appetite in mammals.

The compounds according to formula (I) are suitable for the modulation of the activity of PTPs, in particular of PTP1B. It is therefore believed that the compounds of the present invention are therefore useful for the treatment and/or prevention of disorders which are mediated by PTPs, in particular of PTP1B. Said treatment involves the modulation—notably the down regulation or the inhibition—of PTPs, particularly of PTP1B and/or GLEPP-1.

A further aspect of the present invention is related to a pharmaceutical composition composition a comprising an aryl dicarboxamide according to Formula (I) and at least one further drug (in particular an anti-diabetes agent). In one embodiment the further diabetes agents are selected from the group comprising or consisting of insulin (or insulin mimicks), aldose reductase inhibitors, alpha-glucosidase inhibitors, sulfonyl urea agents, biguanides (e.g. metformin), thiazolidiones (e.g. pioglitazone, rosiglitazone, cf. WO 02/100396) or PPARs agonists or c-Jun Kinase or GSK-3 inhibitors.

Insulins useful with the method of the present invention include rapid acting insulins, intermediate acting insulins, long acting insulins and combination of intermediate and rapid acting insulins.

Aldose reductase inhibitors useful in the method of this invention include those known in the art. These include the non-limiting list of:

a) the spiro-isoquinoline-pyrrolidine tetrone compounds disclosed in U.S. Pat. No. 4,927,831 (Malamas), the contents of which are incorporated herein by reference, which includes ARI-509, also known as minalrestat or Spiro[isoquinoline-4(1H),3'-pyrrolidine]-1,2',3,5'(2H)-tetrone, and analogs thereof, b) 2-[(4-bromo-2-fluorophenyl)methyl]-6-fluoro-(9CI);

c) the compounds of U.S. Pat. No. 4,439,617, the contents of which are incorporated herein by reference, which includes Tolrestat, also known as Glycine, N-[[6-methoxy-5-(trifluoromethyl)-1-naphtalenyl]thioxomethyl]-N-methyl-(9CI) or AY-27773 and analogs thereof, d) Sorbinil (Registra No. 68367-52-2) also known as Spiro[4H-1-benzopyran-4,4'-imidazoline]-2',5'-dione, 6-fluoro-2,3-dihydro-, (4S)-(9CI) or CP 45634;

e) Methosorbinil;

f) Zopolrestat, which is 1-Phtalazineacetic acid, 3,44-dihydro-4-oxo-3-[[5-(trifluoromethyl)-2-benzothiazolyl]methyl]-(9CI) (Registry No. 110703-94-1);

g) Epalrestat, which is 3-Thiazolidineacetic acid, 5-[(2E)-2-methyl-3-phenyl-2-propenylidene]-4-oxo-2-thioxo-, (5Z)-(9CI) Registry No. 82150-09-9);

h) Zenarestat (Registry No. 112733-40-6) or 3-[(4-bromo-2-fluorophenyl)-methyl]-7-chloro-3,4-dihydro-2,4-dioxo-[b 1[1 (2H)-quinazoline acetic acid;

i) Imirestat, also known as 2,7-difluorospiro(9H-fluorene-9, 4'-imidazolidine)-2',5'-dione;

j) Ponalrestat (Registry No. 72702-95-5), which is 1-Phtalazineacetic acid, 3-[(4-bromo-2-fluorophenyl)methyl]3,4-dihydro-4-oxo-(9CI) and also known as Stalil or Statyl;

k) ONO-2235, which is 3-Thiazolidineacetic acid, 5-[(2E)-2-methyl-3-phenyl-2-propenylidene-4-oxo-2-thioxo-, (5Z)-(9CI);

l) GP-1447, which is {3-[(4,5,7-trifluorobenzothiazol-2-yl)methyl]-5-methylphenylacetic acid};

m) CT-112, which is 5-(3-ethoxy-4-pentyloxyphenyl)-2,4-thiazolidinedione;

n) BAL-ARI 8, which is Glycine, N[(7-fluoro-9-oxo-9H-xanthen-2-yl)sulfonyl]-N-methyl-)9CI), Reg. No. 124066-40-6));

o) AD-5467, which is 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI);

p) ZD5522, which is (3',5'-dimethyl-4'-nitromethylsulfonyl-2-(2-tolyl)acetanilide);

q) 3,4-dihydro-2,8-diisopropyl-3-thioxo-2H-1,4-benzoxazine-4-acetic acid;

r) 1-[(3-bromo-2-benzofuranyl)sulfonyl]-2,4-imidazolidinedione (M-16209), s) NZ-314, which is 1-Imidazolidineacetic acid, 3-[(3-nitrophenyl)methyl]-2,4,5-trioxo-9(CI) (Registry No. 128043-99-2), t) 1-phtalazineacetic acid, 3,4-dihydro-4-oxo-3-[(5-trifluoromethyl)-2-benzothiazolyl]-methyl];

u) M-79175, which is Spiro[4H-1-benzopyran-4,4'-imidazolidine]-2',5'-dione; 6-fluoro-2,3-dihydro-2-methyl-, (2R, 4S)-(9CI);

v) SPR-210, which is 2H-1,4-Benzothiazine-2-acetic acid, 3,4-dihydro-3-oxo-4-[(4,5,7-trifluoro-2-benzothiazolyl)methyl]-(9CI);

w) Spiro[pyrrolidine-3,6'(5'H)-pyrrolo[1,2,3-de][1,4]benzoxazine]-2,5,5'-trione, 8-chloro-2'-3'-dihydro-(9CI) (also known as AND 138 or 8-chloro-2',3'-dihydrospiro[pyrolizine-3,6'(5H)-pyrrolo-[1,2,3-de]-[1,4]benzoxazine]2,5,5'-trione);

x) 6-fluoro-2,3-dihydro-2',5'-dioxo-(2S-cis)-spiro[4H-1-benzopyran-4,4'-imidazolidine]-2-carboxamide (also known as SNK-860);

or a pharmaceutically acceptable salt form of one or more of these compounds.

Among the more preferred aldose reductase inhibitors of this invention are minalrestat, Tolrestat, Sorbinil, Methosorbinil, Zopolrestat, Epalrestat, Zenarestat, Imirestat and Ponalrestat or the pharmaceutically acceptable salt forms thereof.

The alpha-glucosidase inhibitors useful for the method of the present invention include miglitol or acarbose, or the pharmaceutically acceptable salt form thereof.

Sulfonylurea agents useful with the method of the present invention include glipizide, Glyburide (Glibenclamide) Clorpropamide, Tolbutamide, Tolazamide and Glimepiride, or the pharmaceutically acceptable salt forms thereof.

Preferably, said supplementary pharmaceutically active agent is selected from the group consisting of a rapid acting insulin, an intermediate acting insulin, a long acting insulin, a combination of intermediate and rapid acting insulins, Inalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol, Acarbose, Glipizide, Glyburide, Chlorpropamide, Tolbutamide, Tolazamide, or Glimepriride.

Still a further object of the invention is a process for preparing aryl dicarboxamides according to formula I.

The aryl dicarboxamides of the present invention may be prepared from readily available starting materials using the below general methods and procedures. It will be appreciated that where typical or preferred experimental conditions (i.e. reaction temperatures, time, moles of reagents, solvents, etc.) are given, other experimental conditions may also be used, unless otherwise stated. Optimum reaction conditions may vary with the particular reactants or solvents used, but such conditions can be determined by one skilled in the art by routine optimisation procedures.

By the following set out general methods and procedures compounds of formula (I) are obtained.

Generally, substituted aryl dicarboxamide derivatives according to the general formula (I) may be obtained by several processes, using both solution-phase and solid-phase chemistry protocols. Depending on the nature of Cy, $R^1$, $R^2$, $R^3$, $R^4$, $R^5$, n, and A, some processes will be preferred to others, this choice of the most suitable process being assumed by the practitioner skilled in the art.

Generally aryl dicarboxamide derivatives of formula (I) may be obtained by the initial deprotection of the precursors (I'), wherein Cy, $R^3$ are as above defined and the moiety FG is A (a substituted or unsubstituted aminocarbonyl moiety) and wherein $R^{4'}$ and $R^{5'}$ can be independently from each other the protected or the non-protected form of $R^4$ and $R^5$ (as above defined) (see Scheme 1 below). For example, when $R^4$ or $R^5$ is a hydroxy group, $R^{4'}$ or $R^{5'}$ can be ether such as OBn, OMe or an ester such as OAc. When $R^4$ or $R^5$ contains a carboxy group, the carboxy groups of $R^{4'}$ or $R^{5'}$ can be an ester such as $CO_2Me$, $CO_2Bn$ or $CO_2tBu$. When $R^4$ (or $R^5$) is a carboxy group and when $R^5$ (or $R^4$) is a hydroxy group, both $R^{4'}$ or $R^{5'}$ groups can be member of a heterocycle such as a substituted 2,2-dimethyl-4-oxo-4H-1,3-benzodioxin-4-one.

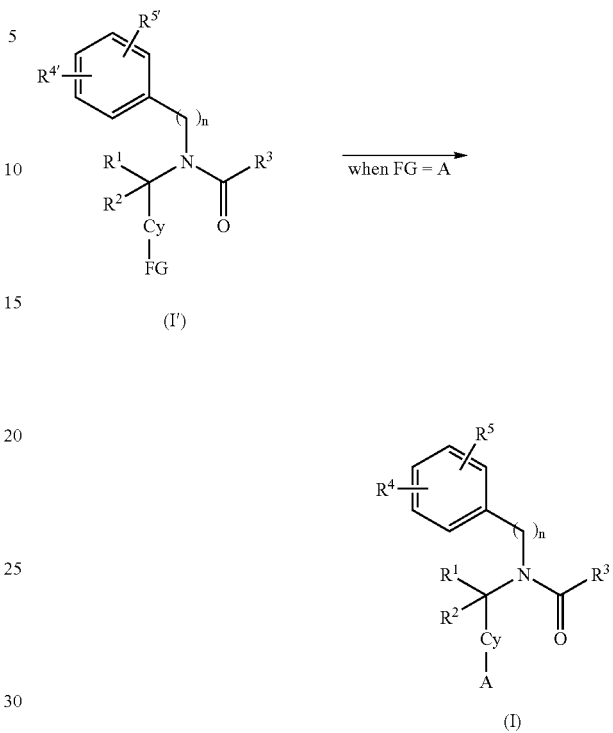

Scheme 1.

It is recognized by those skilled in the art of organic synthesis that the successful use of these methods and of the methods described below is dependent upon the compatibility of substituents on other parts of the molecules. Protecting groups and/or changes in the order of steps described herein may be required.

Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, "Protecting Groups", Georg Thieme Verlag Stuttgart, New York, 1994 and in Theodora W. Greene and Peter G. M. Wuts "Protective Groups in Organic Synthesis", 3rd edition, John Wiley & Sons Inc., 1999 (New York). The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

In the following, the general preparation of aryl dicarboxamide derivatives of formula (I'), wherein Cy, $R^1$, $R^2$, $R^3$, n are as above-defined, wherein $R^{4'}$, $R^{5'}$ may be independently from each other the protected or the non-protected form of $R^4$ and $R^5$ and the moiety FG is A (a substituted or unsubstituted aminocarbonyl moiety), a carboxy, an acyl chloride or a $C_1$-$C_6$-alkyl carboxy group shall be illustrated.

Substituted aryl dicarboxamide derivatives of formula (I') may be prepared by coupling the corresponding amine of formula (II), wherein P is H and wherein Cy, $R^1$, $R^2$, $R^3$, F, n, $R^{4'}$, $R^{5'}$ are as define above, with a carboxylic acid derivatives LG-CO—$R^3$ of formula (III) wherein $R^3$ is as above defined and LG is a suitable leaving group—including OH, Cl, O-alkyl or O-alkylaryl (see Scheme 2 below). A general protocol for such preparation is given below in the Examples, using conditions and methods well known to those skilled in the art to prepare an amide bond from an amine and a carboxylic acid or carboxylic acid derivative (e.g. acyl chloride), with or without standard coupling agents, such as e.g. DIC, EDC, TBTU, DECP, DCC, PyBOP®, Isobutyl chloroformate or others in the presence or not of bases such as TEA, DIEA, NMM in a suitable solvent such as DCM, THF or DMF.

The precursor compounds of formula (II) wherein P is H may be obtained by deprotection of their corresponding protected forms, wherein P is a protecting group such as e.g. Boc or Fmoc.

The precursor compounds of formula (II) wherein P is H or a suitable protecting group, may be prepared from the corresponding precursors of formulae (IV), (V) or (VI), using a variety of synthetic strategies for which some examples are indicated in the below Scheme 3.

Compounds of formula (II)—wherein $R^2$ is H—may for instance be prepared by alkylation of the amines (VII)—wherein $R^{4'}$ and $R^{5'}$ are as above-defined and wherein P is H or a suitable protecting group with the carbonyl derivatives (IV), wherein $R^1$, Cy and FG are as above defined (see Scheme 3, Method A). The reaction may be performed in the presence of a suitable reducing agent including $NaBH(OAc)_3$, $NaBH_3CN$, $NaBH_4$ or hydrogen and an appropriate catalyst such as Pd/C or $PtO_2$.

Alternatively, compounds of formula (II) may be prepared by alkylation of amines of formula (VII)—wherein $R^{4'}$ and $R^{5'}$ are as above-defined and wherein P is H or a suitable protecting group such as e.g. Boc or Fmoc— with the derivatives of formula (V), wherein $LG^1$ is a suitable leaving group including Cl, Br, I, OH, OMs, OTs and wherein $R^1$, $R^2$, Cy and FG are as above-defined (see Scheme 3, Method B).

Also, compounds of formula (II) may be prepared by alkylation of amines of formula (VI), with the alkylating agents of formula (VIII) wherein $LG^1$ is the above-mentioned leaving group (see Scheme 3, Method C).

Still a further alternative is set out in Scheme 3 (Method D). This embodiment illustrates the preparation of compounds of formula (II) by alkylation of the amines of formula (VI) with carbonyl derivatives (IX) in the presence of a reducing agent such as e.g. $NaBH(OAc)_3$, $NaBH_3CN$, $NaBH_4$ or hydrogen with an appropriate catalyst such, as e.g. Pd/C or $PtO_2$, in order to provide compounds of formula (II), wherein n is 1.

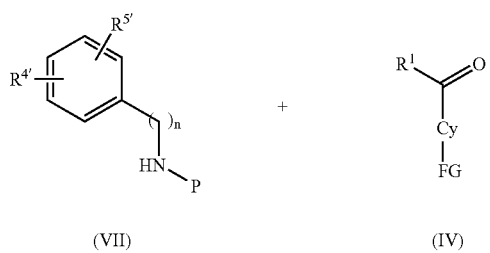

Method A

-continued
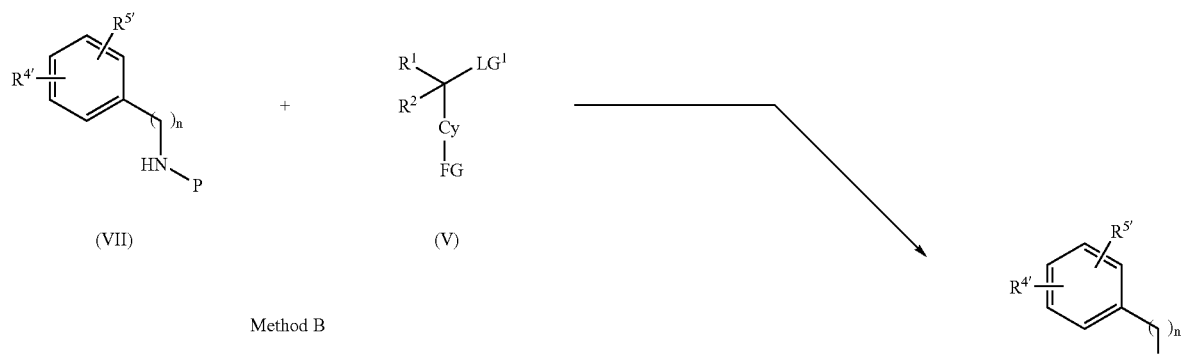
Method B
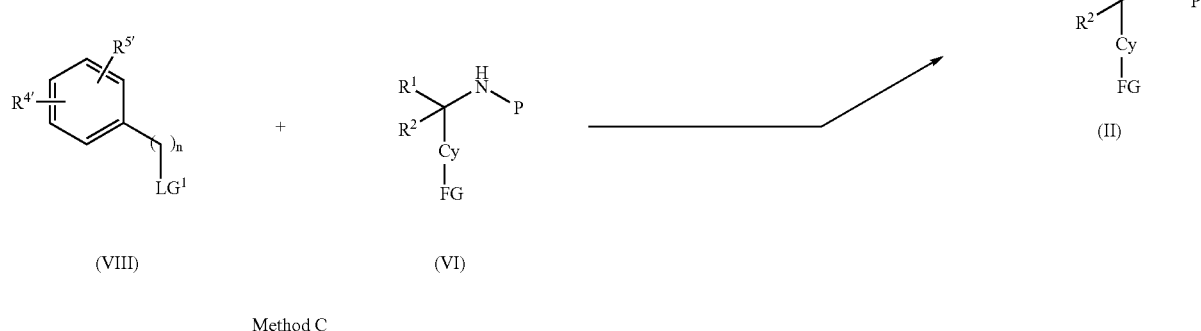
Method C
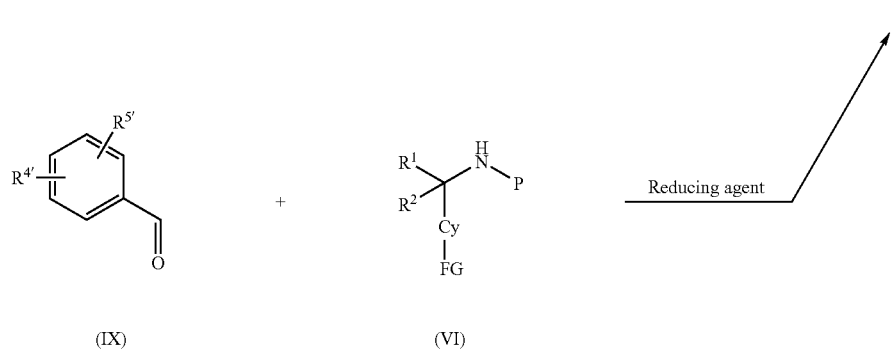
Method D

The precursor compounds of formulae (IV), (V), (VI), (VII), (VIII) or (IX) are either commercially available or readily accessible from commercial starting materials. General protocols for such preparation are given below in the Examples, using conditions and methods well known to those skilled in the art.

The transformation of the moiety FG of the precursors of formulae (I'), (II), (IV), (V) and (VI) wherein $R^1$, $R^2$, Cy, n, P, $R^{4'}$ and $R^{5'}$ are as above defied and wherein FG is a carboxy, an acyl chloride or a $C_1$-$C_6$-alkyl carboxy group, into the precursors of formulae (I'), (II), (IV), (V) and (VI) wherein the moiety FG is A (substituted or unsubstituted aminocarbonyl moiety) can be performed at any stage of the preparation of substituted aryl dicarboxamide derivatives according to the general formula (I) (see Scheme 4 below). It is recognized by those skilled in the art of organic synthesis that the successful use of these methods is dependent upon the compatibility of substituents on others part of the molecules. Protecting group and/or changes in the order of steps described herein may be required.

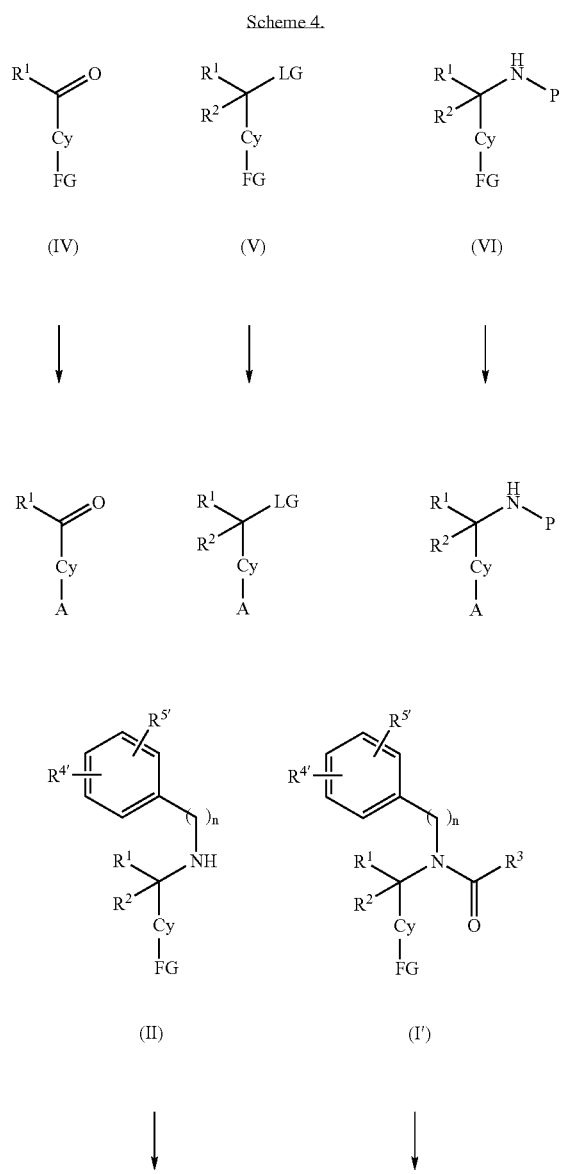

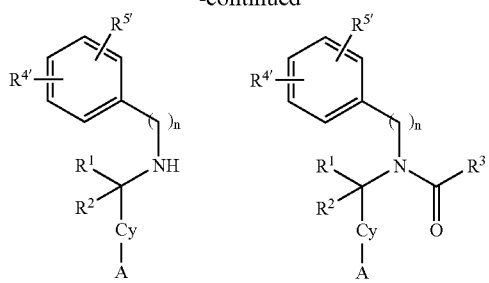

Thus, precursors of formulae (I'), (II), (IV), (V) and (VI) (wherein FG is a carboxy, a $C_1$-$C_6$-alkyl carboxy group, or an acyl chloride group) can be reacted with a primary or secondary amine $HNR^6R^7$ wherein $R^6$, $R^7$ are independently from each other selected from the group consisting of H, $C_1$-$C_6$-alkyl, $C_2$-$C_6$-alkenyl, $C_2$-$C_6$-alkyl, $C_3$-$C_8$-cycloalkyl, heterocycloalkyl, aryl, heteroaryl, $C_1$-$C_6$-alkyl aryl or $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynylheteroaryl, $C_1$-$C_6$-alkyl cycloalkyl, $C_1$-$C_6$-alkyl heterocycloalkyl. A general protocol for such preparation is given below in the Examples, using conditions and methods well known to those skilled in the art to prepare an amide bond from an amine and a carboxylic acid or carboxylic acid derivative (e.g. acyl chloride), with or without standard coupling agents, such as e.g. DIC, EDC, TBTU, DECP, DCC, PyBOP®, Isobutyl chloroformate or others in the presence or not of bases such as TEA, DIEA, NMM in a suitable solvent such as DCM, THF or DMF.

A preferred process for preparing compounds of formula (II) is set out in the above Scheme 3, Method A. Therein, the reductive amination of carbonyl compounds of formula (IV) wherein the moiety FG is A (substituted or unsubstituted aminocarbonyl moiety), with the amines of formula (VII) (P is H) is performed by refluxing them in a suitable solvent (such as toluene with the azeotropic removal of water) to form the intermediate imine followed by its reduction with a reducing agent such as $NaBH_4$ in a suitable solvent such as MeOH. The process thus affords the amine of formula (II) wherein P is H.

According to the methods described in Scheme 2, the resulting amine (II) is coupled with an carboxylic acid derivative (III) such as LG-CO—$R^3$, wherein $R^3$ is as above defined and LG preferably Cl in the presence of a base such as DIEA in an aprotic solvent (such as e.g. DCM or THF), thus affording substituted aryl dicarboxamide derivatives of formula (I'). Subsequent deprotection of $R^{4'}$ and $R^{5'}$ using standard methods and protocols as described below in the Examples affords the desired substituted aryl dicarboxamide derivatives of formula (I). For example, compounds of formula (I') wherein $R^{4'}$ and/or $R^{5'}$ contain an ester group, may be hydrolysed to yield compounds of formula (I) of this invention by their treatment with hydroxide such as e.g. NaOH in an appropriate protic solvent (such as e.g. EtOH), followed by acidification of the reaction mixture.

According to a further preferred process of preparing compounds of formula (I) where $R^4$ is OH and $R^5$ is $CO_2H$, compounds of formula (I'), wherein $R^{4'}$ and $R^{5'}$ are members of a heterocycle such as a substituted 2,2-dimethyl-4-oxo-4H-1,3-benzodioxin-4-one, may be hydrolysed to yield compounds of formula (I) of this invention by their treatment with hydroxide such as e.g. NaOH in an appropriate protic solvent (such as e.g. EtOH) at 70° C., followed by acidification of the reaction mixture.

Basic salts of the compounds of formula (I) are prepared in a conventional manner as is known by those skilled in the art. In particular the N-Me-D-glucamine (i.e. 1-deoxy-1-(methylamino)glucitol) and the tromethamine (i.e. 2-amino-2-(hydroxymethyl)-1,3-propanediol) salts of this invention provide more soluble derivatives in solvents such as water, PBS, PEG, CMC.

The methods of preparation of the substituted methylene amides of formula (I) of this invention according to the above protocols have the specific advantage of being convenient and economic in the sense that they involve only a few steps.

When employed as pharmaceuticals, aryl dicarboxamides of the present invention are typically administered in the form of a pharmaceutical composition. Hence, pharmaceutical compositions comprising a compound of formula (I) and a pharmaceuti-cally acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, aryl dicarboxamides of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the aryl dicarboxamide according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, aryl dicarboxamides of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: h (hour), g (gram), mg (milligram), mmol (millimole), m.p. (melting point), eq (equivalents), mL (milliliter), μL (microliters), ESI (Electro-spray ionization), L (liters), EtOAc (Ethyl acetate), Boc (tert-Butoxycarbonyl), CDCl$_3$ (deuterated chloroform), CD$_3$OD (Deuterated methanol), CH$_3$CN (Acetonitrile), DBU (Diazabicyclo[5.4.0]undec-7-ene), DCC (Dicyclohexyl carbodiimide), DCM (Dichloromethane), DIC (Diisopropyl carbodiimide), DIEA (Diisopropylethylamine), DMAP (4-Dimethylaminopyridine), DMF (Dimethylformamide), DMSO (Dimethylsulfoxide), DMSO-d$_6$ (Deuterated dimethylsulfoxide), EDC (1-(3-Dimethylamino-propyl)-3-ethylcarbodiimide), c-Hex (Cyclohexane), EtOAc (EtOAc), Et$_2$O (Diethyl ether), EtOH (Ethanol), Fmoc (9-Fluorenylmethoxycarbonyl), i-PrOH (2-propanol), K$_2$CO$_3$ (Potassium carbonate), MeOH (Methanol), MgSO$_4$ (Magnesium sulfate), min. (minute), MTBE (Methyl tert-butyl ether), NaHCO$_3$ (Sodium bicarbonate), NaBH$_4$ (Sodium borohydride), NaBH$_3$CN (Sodium cyanoborohydride), NaBH(OAc)$_3$ (Sodium triacetoxyborohydride), NMM (N-methyl-morpholine), Pd(PPh$_3$)$_4$ (Tetrakis triphenylphosphine palladium), PetEther (Petroleum ether), rt (room temperature), PyBOP® (Benzotriazole-1-yl-oxy-tris-pyrrolidino-phosphonium hexafluorophosphate), Rt (retention time), SPE (solid phase extraction), TBTU (2-(1-H-benzotriazole-1-yl)-1,1,3,3-tetramethyluromium tetrafluoroborate), TEA (Triethylamine), TFA (Trifluoroacetic acid), TFAA (Trifluoroacetic acid anhydride), THF (Tetrahydrofuran).

The HPLC, MS and NMR data provided in the examples described below were obtained as followed. HPLC: Waters Symmetry $C_8$ column 50 mm×4.6 mm; UV detection at 254 nm; flow: 2 mL/min; Conditions: 8 min gradient from 0.1% TFA in $H_2O$ to 0.07% TFA in $CH_3CN$. The MS data provided in the examples described below were obtained as followed: Mass spectrum: LC/MS Waters ZMD (ESI). The NMR data provided in the examples described below were obtained as followed: $^1$H-NMR: Bruker DPX-300 MHz.

EXAMPLES

Intermediate I:
7-amino-2,2-dimethyl-4H-1,3-benzodioxin-4-one

Step a) Formation of 4-{[(benzyloxy)carbonyl]amino}-2-hydroxybenzoic acid

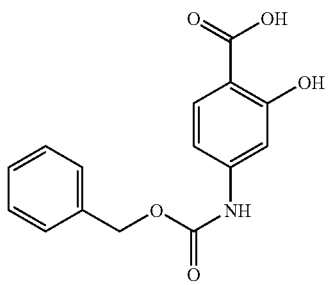

To a solution of sodium-p-aminosalicylate (100 g, 0.65 mol) in 10% aqueous NaOH solution (1 L) was added a 50% wt solution of benzyl chloroformate (670 g, 1.96 mol in toluene) at 0° C. and stirred at rt for 48 h. The reaction mixture was cooled and acidified with a 10% aqueous HCl at 0° C. The solid obtained was filtered and washed with cold water and dried. The solid was treated with PetEther and filtered to give the title compound (128 g, 68%) used in the next steps without further purification.

Step b) Formation of benzyl 2,2-dimethyl-4-oxo-4H-1,3-benzodioxin-7-ylcarbamate

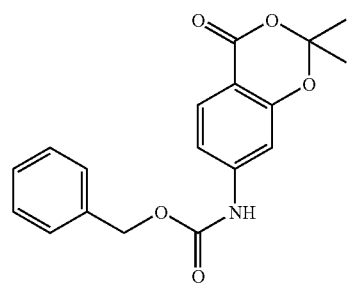

To a suspension of 4-{[(benzyloxy)carbonyl]amino}-2-hydroxybenzoic acid (25 g, 0.087 mol) in TFA (108 mL) was added trifluoroacetic anhydride (TFAA, 35 mL, 0.249 mol) at rt with stirring. To this was added 60 mL of dry acetone in portions (each 4 h interval) and the reaction mixture was refluxed at 60° C. for 24 h. Excess TFA and TFAA was removed under vacuum to give crude product. The crude was purified by column chromatography over silica gel (treated with triethylamine) using $CH_2Cl_2$ as an eluent to give mixture of two compounds: benzyl 2,2-dimethyl-4-oxo-4H-1,3-benzodioxin-7-ylcarbamate (3.5 g) and 7-amino-2,2-dimethyl-4H-1,3-benzodioxin-4-one (1.6 g).

Step c) Formation of
7-amino-2,2-dimethyl-4H-1,3-benzodioxin-4-one

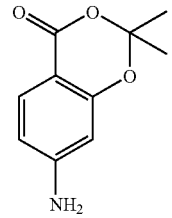

To a solution of benzyl 2,2-dimethyl-4-oxo-4H-1,3-benzodioxin-7-ylcarbamate (3.5 g) in methanol (250 mL) was added Pd/C (350 mg) and hydrogenated under 2 Bars of pressure for 24 h. The reaction mixture was filtered through a bed of celite and concentrated to give the title compound (1.6 g).

Intermediate II:
6-amino-2,2-dimethyl-4H-1,3-benzodioxin-4-one

Step a) Formation of
2,2-dimethyl-6-nitro-4H-1,3-benzodioxin-4-one

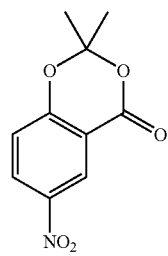

A mixture of 2-hydroxy-5-nitrobenzoic acid (50.0 g, 0.27 mol), acetone (40 mL, 0.54 mol) and trifluoroacetic anhydride (100 mL, 0.71 mol) in TFA (300 mL) was heated at reflux. After 1 hour, a supplementary amount of acetone (60 mL, 0.82 mol) was added and the reaction mixture was refluxed for 48 hours. The solvents were evaporated under reduced pressure. The residual brown solid was dissolved in DCM (800 mL) and washed with a mixture of saturated aqueous $NaHCO_3$ (400 mL) and water (400 mL). The aqueous layer was extracted with DCM (2×400 mL). The combined organic layers were dried over $MgSO_4$ and the solvent was removed under reduced pressure. The residual brown oil was taken up in cold pentane (300 mL, 0° C.) and a yellow solid precipitated off. Filtration and washing with pentane gave 53.8 g (88%) of the title compound as a yellow solid. HPLC, Rt: 2.9 min (purity: 99.8%). $^1$H NMR (CDCl$_3$) δ: 8.88 (d, J=2.8 Hz, 1H), 8.44 (dd, J=9.0, 2.8 Hz, 1H), 7.14 (d, J=9.0 Hz 1H), 1.80 (s, 6H).

Step b) Formation of
6-amino-2,2-dimethyl-4H-1,3-benzodioxin-4-one

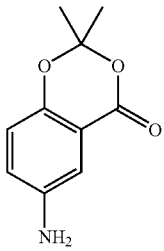

To a solution of 6-nitro-2,2-dimethyl-4H-1,3-benzodioxin-4-one (4.1 g) in EtOH (30 mL) was added Pd/C (1.947 g) under nitrogen atmosphere and then hydrogenated for 12 h at rt. The reaction mixture was filtered through a bed of celite, washed with EtOH and THF. The filtrates were concentrated under vacuum to give the title compound as pale yellow solid (3.5 g, 98%). $^1$H NMR (CDCl$_3$) δ 7.71 (d, J=8.7 Hz, 1H), 7.15 (d, J=2.6 Hz, 1H), 6.83 (dd, J=8.7 Hz, 2.6 Hz, 1H), 3.44 (brs, 2H), 2.63 (s, 6H).

Intermediate III: 6-(aminomethyl)-2,2-dimethyl-4H-1,3-benzodioxin-4-one, acetate salt Step a) Formation of methyl-5-bromosalicylate

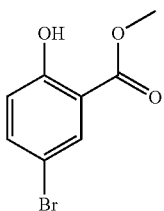

To a solution of 5-bromosalicylic acid (200 g, 0.92 mol) in methanol (2 L) was added thionylchloride (440 g, 3.7 mol) at 0° C. with stirring and then allowed to reflux at 70° C. for 40 h. Excess solvent was distilled off and to the crude residue was added EtOAc (2 L). The organic layer was washed with 10% cold aqueous NaHCO$_3$ solution (2×1 L), brine and dried. The solvent was removed under vacuum to give the title compound as a low melting point solid (190 g, 89%). TLC: PetEther/EtOAc, 7:3, R$_f$: 0.6

Step b) Formation of methyl-5-cyano salicylate

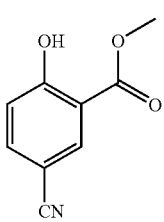

To a solution of methyl-5-bromosalicylate (190 g, 0.822 mol) in dry DMF (1.75 L) was added CuCN (175 g, 1.94 mol) and the reaction mixture was heated to 140° C. with stirring under N$_2$ for 20 h. The reaction mixture was cooled, quenched with water (4 L) and stirred for 45 min. The product was extracted with EtOAc (3×1.5 L), dried and concentrated to give crude product. The aqueous layer was acidified with 1.5 N HCl to pH 3 and further extracted with EtOAc (2×1 L). The combined organic layer was dried and concentrated. The crude product was treated with 10% chloroform in PetEther (200 mL) and the solid filtered off. The solid was further washed with 3% EtOAc in PetEther (200 mL) and dried to give the title compound (80 g, 55%). TLC: PetEther/EtOAc, 8:2, R$_f$: 0.6

Step c) Formation of 5-cyano salicylic acid

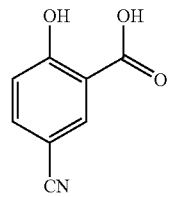

To a suspension of methyl-5-cyano salicylate (80 g, 0.45 mol) in methanol (400 mL), THF (400 mL) and water (200 mL) was added LiOH (32 g, 1.35 mol) and stirred at rt for 20 h. The reaction mixture was concentrated under vacuum, acidified with 1.5 N HCl to pH 3 and the solid obtained filtered off. The solid was dried by azeotropic removal of water using toluene to give the title compound (60 g, 81%). TLC: PetEther/EtOAc, 7:3, R$_f$: 0.1

Step d) Formation of 2,2-dimethyl-4-oxo-4H-1,3-benzodioxine-6-carbonitrile

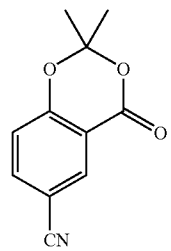

To a suspension of 5-cyano salicylic acid (60 g, 0.368 mol) in TEA (134 mL, 1.76 mol) and TFAA (45 mL, 0.32 mol) was added dry acetone (20 mL) and heated to reflux. After each 1 h interval was added 15 mL of dry acetone for 4 times and the reflux continued for 20 h. The reaction mixture was concentrated under vacuum and crude purified by flash column chromatography over silica gel (230-400 mesh) using CH$_2$Cl$_2$ as an eluent to give the title compound as a white solid (12 g, 15%). TLC: CH$_2$Cl$_2$ (100%), R$_f$: 0.5

Step e) Formation of 6-(aminomethyl)-2,2-dimethyl-4H-1,3-benzodioxin-4-one, acetate salt

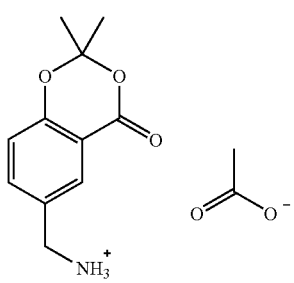

To a solution of 2,2-dimethyl-4-oxo-4H-1,3-benzodioxine-6-carbonitrile (12 g, 0.06 mol) in methanol (500 mL) was added glacial acetic acid (3.5 g, 0.059 mol) and passed $N_2$ for 30 min. To this was added Pd/C (2.4 g, 20%) and hydrogenated under 2 Bars of pressure for 22 h. The reaction mixture was filtered through celite and filtrate concentrated under vacuum. To the solid was added EtOAc (200 mL), stirred for 20 h and filtered. The solid was dried under vacuum to give the title compound (6 g, 38%). TLC: $CHCl_3$/MeOH, 9:1, $R_f$: 0.15

Intermediate IV:
methyl[4-(aminomethyl)phenoxy]acetate, acetate salt

Step a) Formation of methyl(4-formylphenoxy)acetate

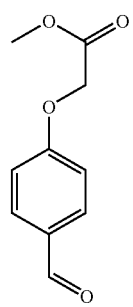

To a solution of 4-hydroxybenzaldehyde (100 g, 0.818 mol) in dry DMF (1 L) was added potassium carbonate (260 g, 1.88 mol) and KI (10 g) with stirring at rt. The reaction mixture was slowly heated to 40° C. and added methylbromoacetate (104 g, 0.67 mol) with stirring and heated to 70° C. for 4 h. The reaction mixture was cooled to rt, filtered off the solid and filtrate was diluted with water (1.5 L). The aqueous mixture was extracted with EtOAc (3×750 mL), washed with 2.5% aqueous NaOH solution (2×400 mL), water and dried. The solvent was removed under vacuum to give the title compound a slight yellow solid (112 g).

Step b) Formation of methyl{4-[(hydroxyimino)methyl]phenoxy}acetate

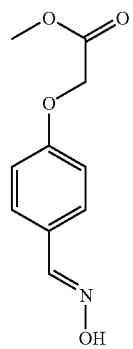

A solution of methyl-(4-formylphenoxy)acetate (100 g, 0.515 mol) in methanol (500 mL) was cooled to 0-5° C. To this was added a solution of hydroxyamine hydrochloride (54 g) and sodium acetate (64 g) in water (500 mL) drop-wise and stirred at rt for 6 h. The reaction mixture diluted with water and filtered off the solid. The solid was washed with water and dried under vacuum to give the title compound (80 g, 74%).

Step c) Formation of methyl[4-(aminomethyl)phenoxy]acetate, acetate salt

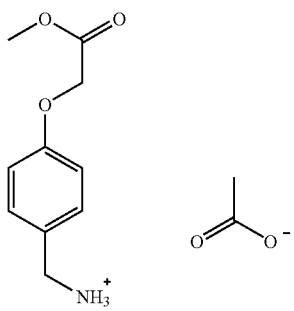

To a solution of methyl{4-[(hydroxyimino)methyl]phenoxy}acetate (30 g, 0.14 mol) in methanol (650 mL) was added glacial acetic acid (6.8 g) and passed $N_2$ for 30 min. To this was added Pd/C (10%, 3 g) and hydrogenated under 2 Bars of pressure for 12 h. The reaction mixture was concentrated under vacuum The crude product was treated with EtOAc (500 mL) and the white product filtered off. The solid was dried under vacuum to give the title compound (29 g, 81%).

Intermediate V:
2-(chloromethyl)-1,3-thiazole-4-carbonyl chloride

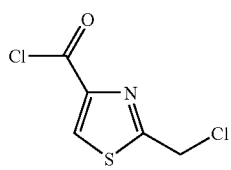

Step a) Formation of ethyl 2-(dichloromethyl)-4,5-dihydro-1,3-thiazole-4-carboxylate Dichloroacetonitrile (33.67 mL, 420 mmol) was added slowly, whilst maintaining the temperature below 0° C., over 30 min. to a solution of sodium methoxide ((25% w/w) 9.63 mL, 43 mmol) in methanol (84.5 mL) which was precooled to −10° C. This was allowd to stir for 30 min. before the addition of L-cysteine ethyl ester hydrochloride (78.32 g, 422 mmol) dissolved in methanol (67.4 mL) and then stirred overnight at RT. Water (136 mL) followed by DCM (136 mL) was added to the mixture and stirred vigorously. The organic layer was separated and the aqueous layer was reextracted with a further 136 mL of DCM. This was concentrated in vacuo to give the crude product (94.1 g, 93%).

Step b) Formation of methyl 2-(chloromethyl)-1,3-thiazole-4-carboxylate

Sodium methoxide (25% w/w in MeOH (44.62 g, 206.5 mmol)) was added slowly, (over 55 min.) whilst maintaining the temperature between 0 and 10° C., to ethyl 2-(dichloromethyl)-4,5-dihydro-1,3-thiazole-4-carboxylate (50.0 g, 206.5 mmol) in 50 mL of MeOH. An additional 50 mL of MeOH was added and stirred for 1 h. keeping the temperature below 10° C. DCM (125 mL) and water (71 mL) was added to the mixture and the organic layer was separated. The aqueous layer was extracted with a further 71 mL of DCM. The combined organic layers was dried over MgSO$_4$ and evaporated in vacuo to give the crude product (34.6 g, 87%).

Step c) Formation of 2-(chloromethyl)-1,3-thiazole-4-carboxylic acid

An aqueous solution of HCl (36%, 68 mL) was added to a solution of methyl 2-(chloromethyl)-1,3-thiazole-4-carboxylate (34 g, 177 mmol) in dioxane (680 mL), water (65 mL) and refluxed overnight. The dioxane was then removed in vacuo and the product was extracted from the aqueous layer with MTBE (4×473 mL), dried over MgSO$_4$ and evaporated to give the title compound (28.3 g, 97%).

Step d) Formation of 2-(chloromethyl)-1,3-thiazole-4-carbonyl chloride

Oxalyl chloride (3.2 mL, 36.6 mmol, 5 eq.) was added dropwise to a suspension of 4-[4-(chloromethyl)-1,3-thiazol-2-yl]benzoic acid (1.30 g, 7.32 mmol, 1 eq.) in DCM (10 mL) followed by a catalytic amount of DMF at RT. The reaction mixture was allowed to stir at RT overnight and then evaporated to give the title compound as the crude product.

Intermediate VI: 4-[4-(chloromethyl)-1,3-thiazol-2-yl]benzoyl chloride

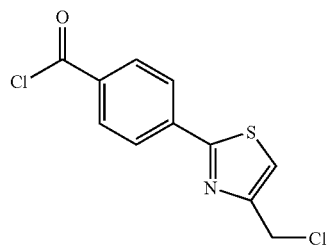

Step a) Formation of methyl 4-(aminocarbonothioyl)benzoate

A mixture of methyl-4-cyanobenzoate (5.0 g, 0.031 mol) and diethyl dithiophosphate (11.5 g, 0.062 mol) in water (100 mL) was stirred overnight at 80° C. under a nitrogen atmosphere. The reaction mixture was allowed to cool to ambient temperatures and the solid was filtered and washed with water (100 mL). The solid was then dried in vacuo at 40° C. to give the crude product (4.74 g, 78%).

Step b) Formation of methyl 4-[4-(chloromethyl)-1,3-thiazol-2-yl]benzoate

A mixture of methyl 4-(aminocarbonothioyl)benzoate (38.48 g, 0.197 mol) 1,3-dichloroacetone (25.05 g, 0.197 mol) in DMF (962 mL) was stirred overnight at 80° C. under an atmosphere of nitrogen. The reaction mixture was allowed to cool to ambient temperatures and then poured into ice water (1000 mL). The solid was filtered, then washed with water (1000 mL) and dried in vacuo at 40° C. to give the crude product (42.7 g, 81%).

Step c) Formation of 4-[4-(chloromethyl)-1,3-thiazol-2-yl]benzoic acid

An aqueous solution of HCl (6N, 200 mL) was added to methyl 4-[4-(chloromethyl)-1,3-thiazol-2-yl]benzoate (20.0 g, 0.075 mol) and refluxed overnight. The reaction mixture was allowed to cool to ambient temperatures and the solid was filtered and then dried in vacuo at 40° C. to give the title compound (15.0 g, 75%).

Step d) Formation of 4-[4-(chloromethyl)-1,3-thiazol-2-yl]benzoyl chloride

Oxalyl chloride (3.2 mL, 36.6 mmol, 5 eq.) was added dropwise to a suspension of 4-[4-(chloromethyl)-1,3-thiazol-2-yl]benzoic acid (1.86 g, 7.32 mmol, 1 eq.) in DCM (10 mL) followed by a catalytic amount of DMF at RT. The reaction mixture was allowed to stir at RT overnight and then evaporated to give the title compound as the crude product.

Procedure A: Solid Phase Synthesis

Step a) Formation of the Resin-Bound Amines

To a round bottomed flask fitted with stirrer and nitrogen inlet was added AMEBA II resin (or the like such as PS-MB-CHO HL 100-200 mesh purchased from from Argonaut Technologies Inc.), 50 g (0.96 mmol/g, 0.048 mol). A mixture of THF/TMOF (9:1, 500 mL) was added. Primary amines e.g. 4-phenoxybenzylamine (1.5 eq., 0.072 mol) was added to the flask. Acetic acid (2.75 mL, 1.5 eq.) was then added and the reaction mixture stirred for 1 h. Sodium triacetoxyborohydride (15.25 g, 0.072 mol, 1.5 eq.) was added to the flask and the reaction stirred overnight at RT under nitrogen The excess hydride was neutralized with an aqueous solution of NaOH (2M, 20 mL) and the polymer was recovered by filtration. The polymer was washed with DMF (250 mL), water (250 mL), DMF (250 mL), water (250 mL), acetone (250 mL), methanol (250 mL), acetone (250 mL), methanol (250 mL), dried under vacuo at 60° C. to afford the resin-bound amine which was used directly in the next step.

Step b) Formation of the Resin-Bound Amides

DIEA (294 µL, 1.69 mmol) was added to a suspension of the resin (750 mg, 0.56 mmol) and acid chloride (such as 4-[4-(chloromethyl)-1,3-thiazol-2-yl]benzoyl chloride, 1-5 eq., typically 1.5 eq.) in DCM (8 mL) and shaken overnight at ambient temperatures. The resin was then washed using the standard washing cycle (2×DMF, 2×DCM, 2×DMF, 2×DCM, 2×MeOH, 2×DCM, 2×MeOH) and dried in a vacuum oven at 40° C. for 1 h to afford the resin-bound amide which was used directly in the next step.

Step c) Formation of the Resin-Bound Secondary Amines

DIEA (0.805 mL, 4.62 mmol, 10 eq.) and amine (2.31 mmol, 5 eq.) were added to a suspension of resin (described in step b, 1 eq., 660 mg, 0.462 mmol). When amines are the intermediate III or IV, TBAI (511 mg, 1.69 mmol, 3 eq.) was added. When amines are intermediate I, II, KI (76.7 mg, 0.462 mmol, 1 eq.) was added instead of TBAI. The resin was then washed following the standard washing cycle and dried to afford the resin-bound secondary amine which was used directly in the next step.

Step d) Formation of the Resin-Bound Amides 0.5 mL of a solution of DIEA (5 eq, 0.193 mmol) in DCM was added to the resin (described in step c, 1 eq.), followed by 0.5 mL of a stock solution of the acid chloride (5 eq, 0.193 mmol) in DCM and shaken overnight at ambient temperatures. The resin was then washed following the standard washing cycle and dried to afford the resin-bound amide which was used directly in the next step.

Step e) Formation of the Resin-Bound Carboxylic Acids

This step was performed only when intermediate IV was used in step d.

1 mL of a stock solution of TMSOK in THF (0.19 mmol/mL, 5 eq.) was added to the resin (55 mg, 0.039 mmol) and shaken overnight at RT. The resin was then washed, firstly with water and then following the standard washing cycle and then dried to afford the resin-bound carboxylic acid which was used directly in the next step Step f) Cleavage from the Resin The resin-bound carboxylic acids (described in step e, 1 eq.) or the resin bound amides (described in step d, 1 eq.) was poured in a mixture of TFA/DCM (05/95-20/80, typically 10/90, 1 mL for 100 mg of resin) for 1 h at rt. Evaporation of the solvents under vacuum gave the title compound when the intermediate IV was used in the step d or the protected form of title compound (as a substituted 2,2-dimethyl-4-oxo-4H-1,3-benzodioxin-4-one derivative) when the intermediate I, II or III was used in the step d.

Step g) Deprotection of the substituted 2,2-dimethyl-4-oxo-4H-1,3-benzodioxin-4-one This step was performed only when intermediate I, II, or III was used in step d.

1 mL of a solution of TFA/H$_2$O was added to the compound obtained in step e and shaken for 48 h. at RT. The solvents were evaporated in vacuo to give the title compound.

Example 1

5-[(3-cyclopentylpropanoyl)(4-{[(4-phenoxybenzyl)amino]carbonyl}benzyl)amino]-2-hydroxybenzoic acid Step a) Formation of benzyl 4-{[(2,2-dimethyl-4-oxo-4H-1,3-benzodioxin-6-yl)amino]-methyl}benzoate

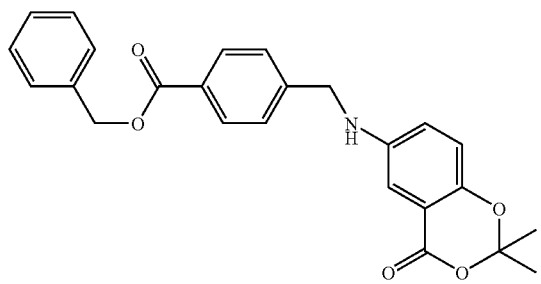

A solution of 4-formylbenzoate (481 mg) and 6-amino-2,2-dimethyl-4H-1,3-benzodioxin-4-one (386 mg) in toluene (20 mL) was heated at reflux for 12 h with azeotropic removal of water. The toluene was evaporated off under reduce pressure, the residue was taken up in methanol (10 mL) and cooled to 0° C. NaBH$_4$ (114 mg) was added portionwise and the reaction mixture was stirred at 0° C. for 1 h then at rt for 2 h. The reaction mixture was poured into water and resulting mixture extracted with Et$_2$O. The combined organic layers were washed with brine, dried over MgSO$_4$ and filtered. The solvent was removed under reduce pressure to give the crude product as an oil. The product was purified by flash chromatography (SiO$_2$, EtOAc/c-Hex 20/80) to give the title compound as a colorless oil (713 mg, 85%). $^1$H NMR (CDCl$_3$) δ 8.07 (d, J=8.1 Hz, 2H), 7.54-7.32 (m, 7H), 7.17 (d, J=2.6 Hz, 1H), 6.89-6.78 (m, 2H), 5.37 (s, 2H), 4.41 (s, 2H), 1.70 (s, 6H). M$^+$(ESI): 418.3; M$^-$(ESI): 416.1. HPLC, Rt: 4.6 min (purity: 95.8%).

Step b) Formation of benzyl 4-{[(3-cyclopentylpropanoyl)(2,2-dimethyl-4-oxo-4H-1,3-benzodioxin-6-yl)amino]methyl}benzoate

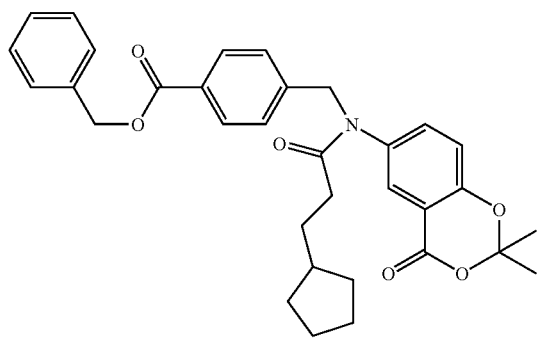

To a cold (0° C.) solution of benzyl 4-{[(2,2-dimethyl-4-oxo-4H-1,3-benzodioxin-6-yl)amino]methyl}benzoate (430 mg) and DIEA (146 mg) in anhydrous DCM (5 nm) was added a solution of 3-cyclopentylpropanoyl chloride (182 mg, 1 M in DCM). The mixture was stirred 1 h at 0° C. then 3 h at rt. An aqueous solution of HCl (1N, 50 mL) was added and the resulting mixture was extracted with Et$_2$O (3×50 mL). The combined organic layers were washed with brine (1×50 mL), dried over MgSO$_4$, filtered and evaporated under vacuum to give a light orange oil. Purification by chromatography (SiO$_2$, DCM/c-Hex) gave the title compound as a colorless oil (499 mg, 89%). $^1$H NMR (CDCl$_3$) δ 8.00 (d, J=8.3 Hz, 2H), 7.69 (d, J=2.3 Hz, 1H), 7.49-7.32 (m, 5H), 7.27 (d, J=7.5 Hz, 2H), 7.11-7.03 (m, 1H), 6.91 (d, J=8.6 Hz, 1H), 5.37 (s, 2H), 4.93 (s, 2H), 2.13-2.05 (m, 2H), 1.85 (s, 6H), 1.71-1.37 (m, 9H), 1.06-0.89 (m, 2H). M$^+$(ESI): 542.3.

Step c) Formation of 4-{[(3-cyclopentylpropanoyl)(2,2-dimethyl-4-oxo-4H-1,3-benzodioxin-6-yl)amino]methyl}benzoic acid

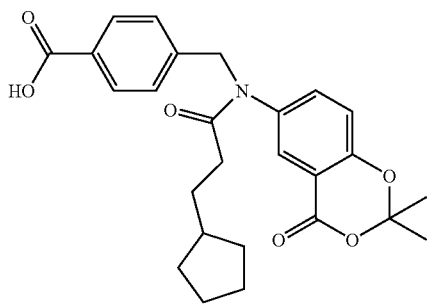

H$_2$ (1 atm) was bubbled slowly trough a suspension of 10% Pd/C (106 mg) in EtOH (10 mL) for 15 min at rt. To this suspension was then added a solution of benzyl 4-{[(3-cyclopentylpropanoyl)(2,2-dimethyl-4-oxo-4H-1,3-benzodioxin-6-yl)amino]methyl}benzoate (480 mg) diluted in EtOH (5 mL). The resulting reaction mixture was stirred under 1 atm H$_2$ for 5 h at rt. The solution was degassed by passing N$_2$ through the solution. The reaction mixture was filtered over a pad of celite and the solvent was evaporated to afford the title compound as a white solid (399 mg, 99%) used in the next steps without further purification. $^1$H NMR (CDCl$_3$) δ 7.95 (d, J=8.3H, 2H), 7.63 (d, J=2.5 Hz, 1H), 7.22 (d, J=7.2 Hz, 2H), 7.06-6.97 (m, 1H), 6.85 (d, J=8.7 Hz, 1H), 4.87 (s, 2H), 2.03 (t, J=7.2 Hz, 2H), 1.67 (s, 6H), 1.67-1.28 (m, 9H), 0.97-0.79 (m, 2H). M$^+$(ESI): 452.4; M$^-$(ESI): 450.4. HPLC, Rt: 4.3 min (purity: 96.7%).

Step d) Formation of 4-{[(3-cyclopentylpropanoyl)(2,2-dimethyl-4-oxo-4H-1,3-benzodioxin-6-yl)amino]methyl}-N-(4-phenoxybenzyl)benzamide

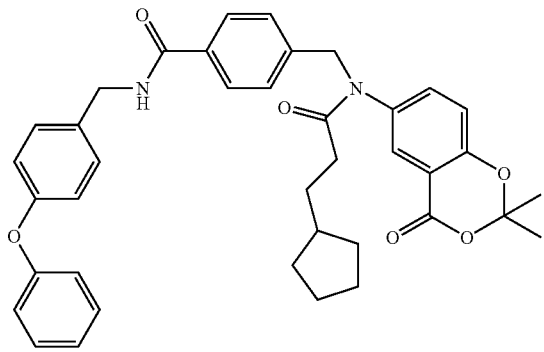

To a solution of 4-{[(3-cyclopentylpropanoyl)(2,2-dimethyl-4-oxo-4H-1,3-benzodioxin-6-yl)amino]methyl}benzoic acid (212 mg) in THF (2 mL) was added NMM (57 mg). The mixture was chilled at 0° C. and isobutyl chloroformate was added at once (86 mg). The mixture was stirred for 15 min. at 0° C. then 4-phenoxybenzylamine (103 mg) was added and the resulting reaction mixture was stirred 3 h at rt. An aqueous solution oh HCl (1N, 2 mL) was added and the resulting mixture was extracted with Et$_2$O. The combined organic layers were washed with water, brine, dried over MgSO$_4$ filtered and evaporated to give a light yellow oil. Purification by chromatography (SiO$_2$) gave the title compound as a colorless oil (241 mg, 81%). $^1$H NMR (CDCl$_3$) δ 7.56-7.42 (m, 3H), 7.21-7.00 (m, 6H), 6.95-6.67 (m, 7H), 6.21 (t, J=4.9 Hz, 1H), 4.69 (s, 2H), 4.42 (s, 1H), 4.40 (s, 1H), 1.87 (t, J=7.2 Hz, 2H), 1.54 (s, 6H), 1.48-1.14 (m, 9H), 0.85-0.64 (m, 2M). M$^+$(ESI): 633.0; M$^-$(ESI): 631.0. HPLC, Rt: 5.3 min (purity: 97.7%).

Step e) Formation of 5-[(3-cyclopentylpropanoyl)(4-{[(4-phenoxybenzyl)amino]carbonyl}-benzyl)amino]-2-hydroxybenzoic acid

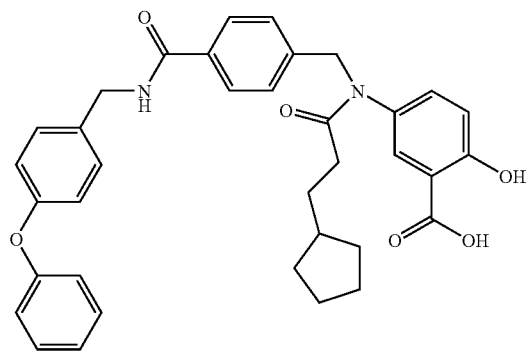

To a solution of 4-{[(3-cyclopentylpropanoyl)(2,2-dimethyl-4-oxo-4H-1,3-benzodioxin-6-yl)amino]methyl}-N-(4-phenoxybenzyl)benzamide (200 mg) in EtOH (3 mL) was added an aqueous solution (0.071 mL, 1N). The mixture was heated at 70° C. for 3 h. After cooling to rt, an aqueous solution of HCl (2 mL, 1N) was added and the resulting reaction mixture was extracted (EtOAc). The combined organic layers were washed with water, brine, dried over MgSO$_4$, filtered and evaporated to give the title compound as a white powder (160 mg, 85%). $^1$H NMR (DMSO-d) δ 8.99 (t, J=6.0 Hz, 1H), 7.82 (d, J=8.2 Hz, 2H), 7.50 (d, J=2.6 Hz, 1H), 7.42-7.06 (m, 8H), 7.03-6.89 (m, 5H), 4.85 (s, 2H), 4.45 (s, 1H), 4.43 (s, 1H), 3.40 (brs, 1H), 2.05 (t, J=7.5 Hz, 2H), 1.70-1.32 (m, 9H), 1.00-0.81 (m, 2H). M$^+$(ESI): 593.0; M$^-$(ESI): 591.0. HPLC, Rt: 4.9 min purity: 99.3%).

Example 2

5-[(3-cyclopentylpropanoyl)(4-{[(4-phenoxybenzyl)amino]carbonyl}-benzyl)amino]-2-hydroxybenzoic acid, N-methyl-D-glucamine (i.e. 1-deoxy-1-(methylamino)glucitol) salt

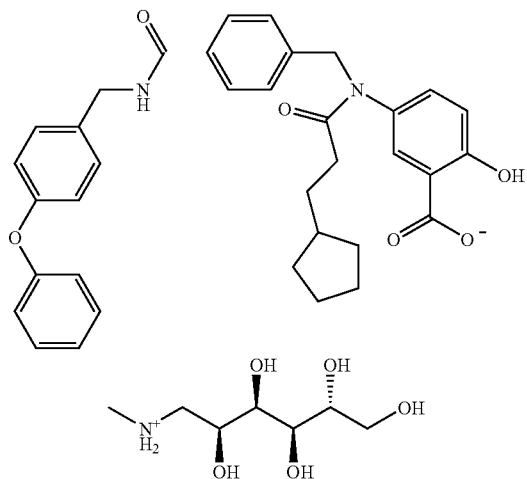

To a solution of 5-[(3-cyclopentylpropanoyl)(4-{[(4-phenoxybenzyl)amino]carbonyl}benzyl)amino]-2-hydroxybenzoic acid (80 mg, 0.135 mmol) in EtOH (5 mL) was added N-methyl-D-glucamine (26.4 mg, 0.135 mmol). The resulting mixture was sired until a homogeneous solution was obtained. The solvent was removed in vacuum and the residue was dissolved in a 9/1 mixture of H$_2$O/EtOH. The resulting solution was then lyophilized to afford the title compound as a white powder (70 mg). M$^+$(ESI): 593.0; M$^-$(ESI): 591.0. HPLC, Rt: 4.9 min (purity: 97.0%).

Example 3

[4-({{[2-(4-{[(4-pentylbenzyl)amino]carbonyl}phenyl)-1,3-thiazol-4-yl]methyl}[(2E)-3-phenylprop-2-enoyl]amino}methyl)phenoxy]acetic acid

Step a) Formation of 4-[4-(chloromethyl)-1,3-thiazol-2-yl]-N-(4-pentylbenzyl)benzamide

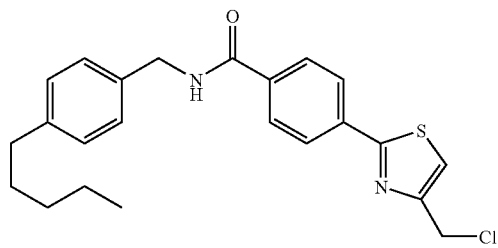

N-methylmorpholine (1.7 mL, 15.3 mmol) and isobutyl chloroformate (1.0 mL, 7.65 mmol) were added to a solution of 4-[4-(chloromethyl)-1,3-thiazol-2-yl]benzoic acid (1.85 g, 7.29 mmol) in anhydrous THF (30 mL) at 0° C. The reaction mixture was stirred at 0° C. for 30 min, then (4-pentylbenzyl)amine hydrochloride (1.64 g, 7.65 mmol) was added neat. The reaction mixture was stirred for 15 min at 0° C., then 2 hours at RT. The reaction mixture was diluted with DCM (100 mL) and washed with 1M aqueous HCl (50 mL), then saturated aqueous NaHCO$_3$ (50 mL). The aqueous layers were extracted with DCM (100 mL). The combined organic layers were dried over MgSO$_4$ and the solvents were removed under reduced pressure to give a brown solid. Recrystallization from a mixture MeOH/water gave 2.30 g (75%) of the title compound as beige solid. HPLC, Rt: 5.2 min (purity: 98.0%). $^1$H NMR (CDCl$_3$) δ: 8.01 (d, J=8.3 Hz, 2H), 7.86 (d, J=8.3 Hz, 2H), 7.37 (s, 1H), 7.30 (d, J=8.0 Hz, 2H), 7.19 (d, J=8.0 Hz, 2H), 6.47 (m, 1H), 4.76 (s, 2H), 4.63 (d, J=5.5 Hz, 2H), 2.61 (t, J=7.7 Hz, 2H), 1.63 (m, 2H), 1.34 (m, 4H), 0.90 (t, J=6.8 Hz, 3H).

Step b) Formation of methyl{4-[({[2-(4-{[(4-pentylbenzyl)amino]carbonyl}phenyl)-1,3-thiazol-[b 4[1 yl]methyl}amino)methyl]phenoxy}acetate, hydrochloride salt

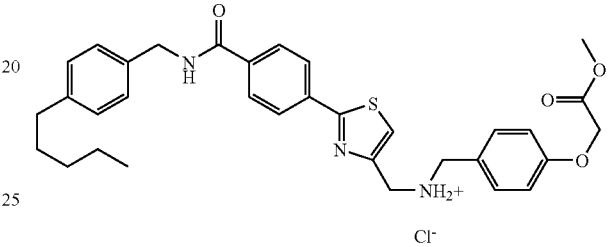

A solution of 4-[4-(chloromethyl)-1,3-thiazol-2-yl]-N-(4-pentylbenzyl)benzamide (500 mg, 1.21 mmol) and Bu$_4$NI (450 mg, 1.21 mmol) in anhydrous THF (5 mL) was added to a refluxed solution of methyl[4-(aminomethyl)phenoxy]acetate, acetate salt (620 mg, 2.42 mmol) and TEA (500 µL, 3.63 mmol). The reaction mixture was stirred under reflux for 3.5 hours, then the solvent was removed under reduced pressure. The residue was taken off with saturated aqueous NaHCO$_3$ (50 mL) and extracted with DCM (100 mL+2×50 mL). The combined organic layers were dried over Na$_2$SO$_4$ and the solvent was removed under reduced pressure. Purification by flash chromatography (DCM/MeOH 95:5), followed by precipitation of the hydrochloride salt (HCl 1.25M/MeOH in MeOH, 0° C.) gave 201 mg (30%) of the title compounds as a white solid. M$^+$(ESI): 572.3; M$^-$(ESI): 570.6. HPLC, Rt: 4.1 min (purity: 99.9%). $^1$H NMR (DMSO-d$_6$) δ: 9.51 (brs, 2H), 9.16 (t, J=5.9 Hz, 1H), 8.08 (d, J=8.7 Hz, 2H), 8.03 (d, J=8.7 Hz, 2H), 7.94 (s, 1H), 7.47 (d, J=8.7 Hz, 2H), 7.23 (d, J=7.9 Hz, 2H), 7.14 (d, J=7.9 Hz, 2H), 7.00 (d, J=8.7 Hz, 2H), 4.82 (s, 2H), 4.45 (d, J=5.9 Hz, 2H), 4.30 (s, 2H), 4.20 (s, 2H), 3.69 (s, 3H), 2.54 (t, J=7.6 Hz, 2H), 1.53 (m, 2H), 1.27 (m, 4H), 0.84 (t, J=6.8 Hz, 3H).

Step c) Formation of methyl[4-({{[2-(4-{[(4-pentylbenzyl)amino]carbonyl}phenyl)-1,3-thiazol-4-yl]methyl}[(2E)-3-phenylprop-2-enoyl]amino}methyl)phenoxy]acetate

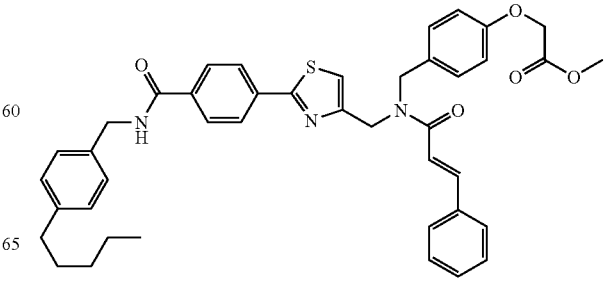

Cinnamyl chloride (77 mg, 0.46 mmol) was added neat to a solution of methyl {4-[({[2-(4-{[(4-pentylbenzyl)amino]carbonyl}phenyl)-1,3-thiazol-4-yl]methyl}amino)methyl]phenoxy}acetate, hydrochloride salt (168 mg, 0.28 mmol) in anhydrous pyridine (5 mL) at 0° C. The resulting mixture was stirred for 10 min at 0° C. and 30 ml at RT. Then PL-AMS-Resin (Polymer Laboratories, 1.93 mmol/g, 300 mg) was added and the mixture was stirred at RT for 45 min. After filtration of the resin, the mixture was diluted with 1M aqueous HCl (100 mL) and extracted with DCM (2×100 mL). The combined organic layers were dried over MgSO$_4$ and the solvent was removed under reduced pressure. Purification by flash chromatography (DCM/MeOH 95:5) gave 182 mg (94%) of the title compound as colorless oil. M$^+$(ESI): 702.0; M$^-$(ESI): 700.0. HPLC, Rt: 5.7 min (purity: 100%). $^1$H NMR (CDCl$_3$) δ: 8.01 (m, 2H), 7.84 (m, 3H), 7.50 (m, 2H), 7.39-6.94 (m, 11H), 6.88 (m, 2H), 6.46 (m, 1H), 4.89 (s, 1H), 4.87 (s, 1H), 4.77 (s, 1H), 4.75 (s, 1H), 4.62 (m, 4H), 3.81 (s, 1.5H), 3.79 (s, 1.5H), 2.61 (t, J=7.7 Hz, 2H), 1.62 (m, 2H), 1.33 (m, 4H), 0.90 (t, J=6.8 Hz, 3H).

Step d) Formation of [4-({{[2-(4-{[(4-pentylbenzyl)amino]carbonyl}phenyl)-1,3-thiazol-4-yl]methyl}[(2E)-3-phenylprop-2-enoyl]amino}methyl)phenoxy]acetic acid

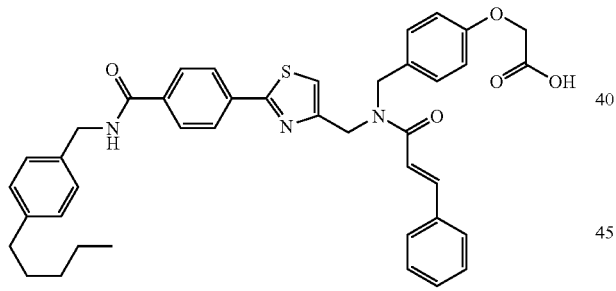

1N aqueous NaOH (0.5 mL) was added to a solution of methyl[4-({{[2-(4-{[(4-pentylbenzyl)amino]

carbonyl}phenyl)-1,3-thiazol-4-yl]methyl}[(2E)-3-phenylprop-2-enoyl]amino}methyl)phenoxy]acetate (163 mg, 0.23 mmol) in MeOH (5 mL). The reaction mixture was stirred at RT for 2 hours, then poured into 1N aqueous HCl (25 mL). The resulting precipitate was filtered, washed with water (3×) and dried under reduced pressure to give 120 mg (75%) of the title compound as a white solid. M$^+$(ESI): 688.1; M$^-$(ESI): 686.5. HPLC, Rt: 5.3 min (purity: 100%). $^1$H NMR (CDCl$_3$) δ: 7.97-7.79 (m, 5H), 7.50-7.01 (m, 13H), 6.84 (m, 2H), 6.57 (m, 1H), 4.88 (brs, 2H), 4.75 (brs, 2H), 4.60 (m, 4H), 2.60 (t, J=7.7 Hz, 2H), 1.61 (m, 2H), 1.33 (m, 4H), 0.90 (t, J=6.4 Hz, 3H).

Example 4

5-[(3-cyclopentylpropanoyl)(4-{[(4-pentylbenzyl)amino]carbonyl}benzyl)amino]-2-hydroxybenzoic acid

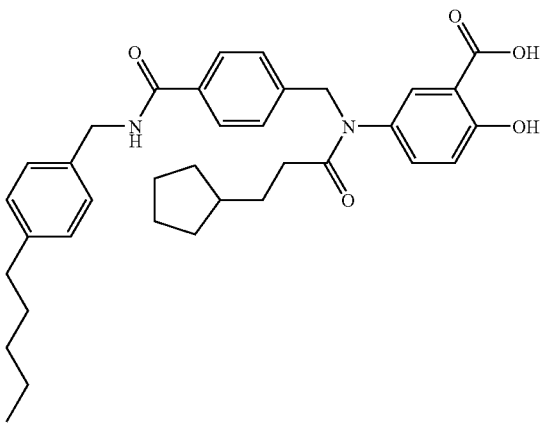

The title compound was prepared following the procedure A using 4-pentylbenzylamine, 4-(chloromethyl)benzoyl chloride, 3-cyclopentylpropanoyl chloride and 6-amino-2,2-dimethyl-4H-1,3-benzodioxin-4-one. M$^+$(ESI): 571.6

Example 5

2-hydroxy-5-{(4-{[(4-pentylbenzyl)amino]carbonyl}benzyl[4-(trifluoromethyl)benzoyl]amino}benzoic acid

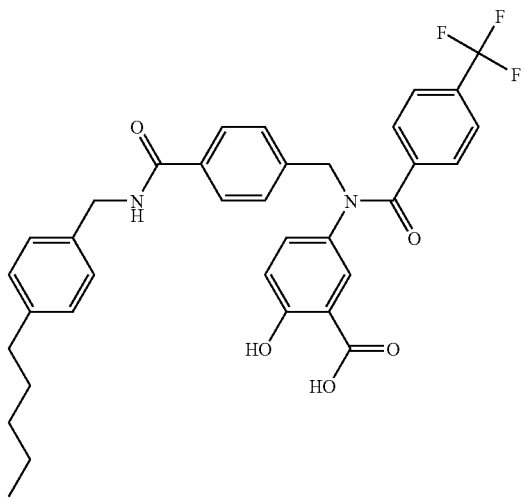

The title compound was prepared following the procedure A using 4-pentylbenzylamine, 4-(chloromethyl)benzoyl chloride, 4-(trifluoromethyl)benzoyl chloride and 6-amino-2,2-dimethyl-4H-1,3-benzodioxin-4-one. M$^+$(ESI): 619.6

Example 6

2-hydroxy-5-[[(4-{[(4-phenoxybenzyl)amino]carbonyl}-1,3-thiazol-2-yl)methyl[9 (3-phenylpropanoyl)amino]benzoic acid

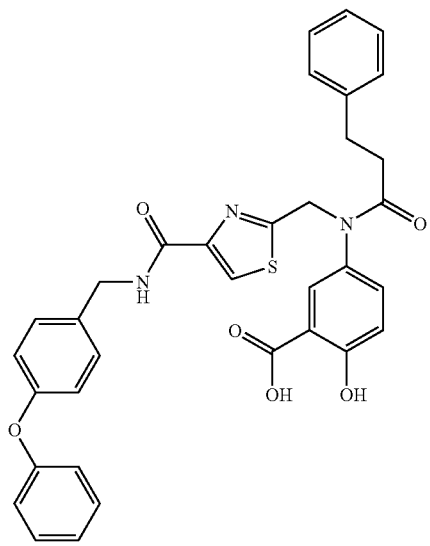

The title compound was prepared following the procedure A using 4-phenoxybenzylamine, 2-(chloromethyl)-1,3-thiazole-4-carbonyl chloride, 3-phenylpropanoyl chloride and 6-amino-2,2-dimethyl-4H-1,3-benzodioxin-4-one. M$^+$(ESI): 608.8

Example 7

5-{benzoyl[(4-{[(4-phenoxybenzyl)amino]carbonyl}-1,3-thiazol-2-yl)methyl]amino}-2-hydroxybenzoic acid

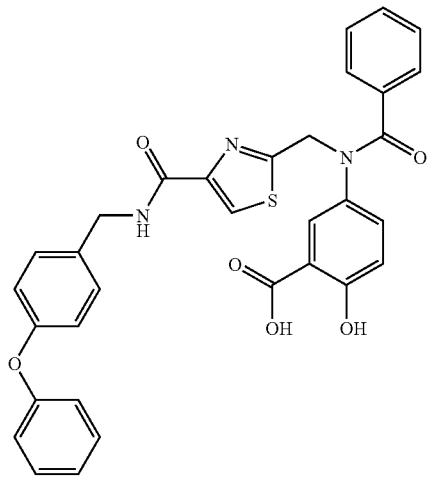

The title compound was prepared following the procedure A using 4-phenoxybenzylamine, 2-(chloromethyl)-1,3-thiazole-4-carbonyl chloride, benzoyl chloride and 6-amino-2,2-dimethyl-4H-1,3-benzodioxin-4-one. M$^+$(ESI): 580.9

Example 8

2-hydroxy-5-{[(4-{[(4-phenoxybenzyl)amino]carbonyl}-1,3-thiazol-2-yl)methyl][4-(trifluoromethyl)benzoyl]amino}benzoic acid

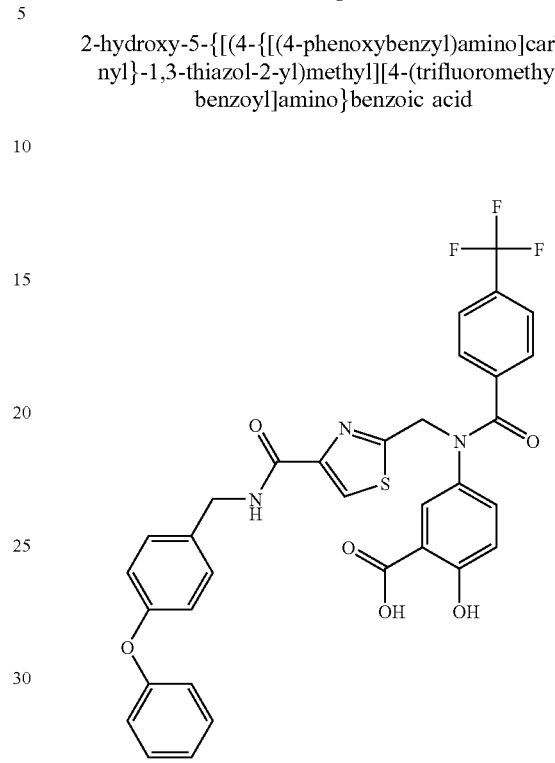

The title compound was prepared following the procedure A using 4-phenoxybenzylamine, 2-(chloromethyl)-1,3-thiazole-4-carbonyl chloride, 4-(trifluoromethyl)benzoyl chloride and 6-amino-2,2-dimethyl-4H-1,3-benzodioxin-4-one. M$^+$(ESI): 648.0

Example 9

5-[(cyclohexylcarbonyl)(4-{[(4-phenoxybenzyl)amino]carbonyl}benzyl)-amino]-2-hydroxybenzoic acid

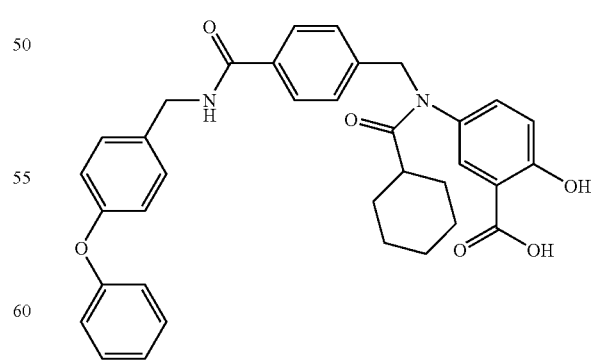

The title compound was prepared following the procedure A using 4-phenoxybenzylamine, 4-(chloromethyl)benzoyl chloride, cyclohexanecarbonyl chloride and 6-amino-2,2-dimethyl-4H-1,3-benzodioxin-4-one. M$^+$(ESI): 579.1

Example 10

2-hydroxy-5-[(4-{[(4-phenoxybenzyl)amino]carbonyl}benzyl)(3-phenylpropanoyl)amino]benzoic acid

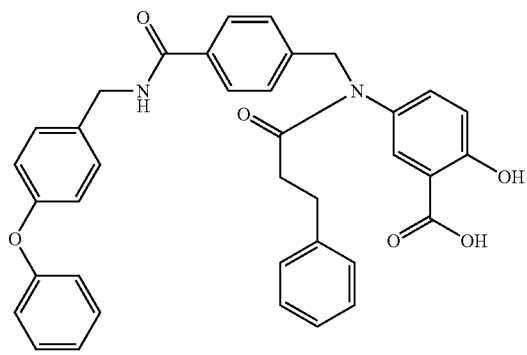

The title compound was prepared following the procedure A using 4-phenoxybenzylamine, 4-(chloromethyl)benzoyl chloride, 3-phenylpropanoyl chloride and 6-amino-2,2-dimethyl-4H-1,3-benzodioxin-4-one. $M^+$(ESI): 601.1

Example 11

5-[benzoyl(4-{[(4-phenoxybenzyl)amino]carbonyl}benzyl)amino]-2-hydroxybenzoic acid

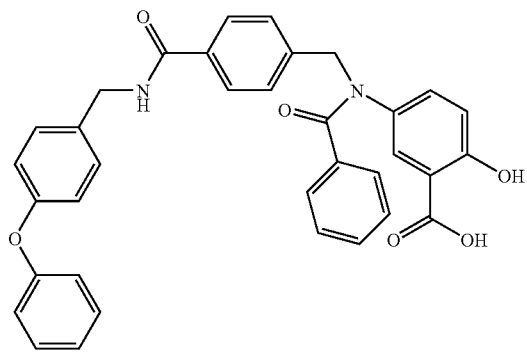

The title compound was prepared following the procedure A using 4-phenoxybenzylamine, 4-(chloromethyl)benzoyl chloride, benzoyl chloride and 6-amino-2,2-dimethyl-4H-1,3-benzodioxin-4-one. $M^+$(ESI): 573.1

Example 12

5-[acetyl(4-{[(4-phenoxybenzyl)amino]carbonyl}benzyl)amino]-2-hydroxybenzoic acid

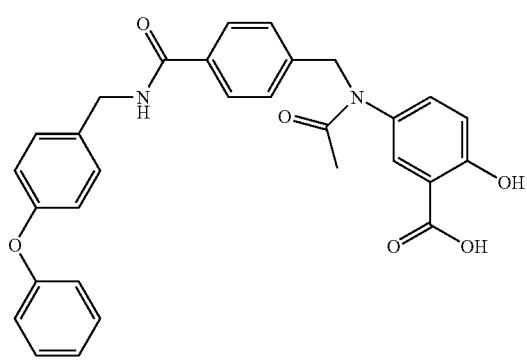

The title compound was prepared following the procedure A using 4-phenoxybenzylamine, 4-(chloromethyl)benzoyl chloride, acetyl chloride and 6-amino-2,2-dimethyl-4H-1,3-benzodioxin-4-one. $M^+$(ESI): 511.1

Example 13

5-[(4-cyanobenzoyl)(4-{[(4-phenoxybenzyl)amino]carbonyl}benzyl)amino]-2-hydroxybenzoic acid

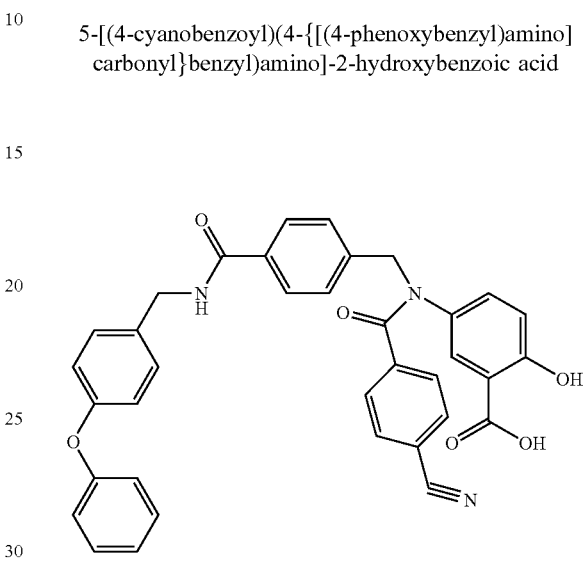

The title compound was prepared following the procedure A using 4-phenoxybenzylamine, 4-(chloromethyl)benzoyl chloride, 4-cyanobenzoyl chloride and 6-amino-2,2-dimethyl-4H-1,3-benzodioxin-4-one. $M^+$(ESI): 598.1

Example 14

2-hydroxy-5-[(phenoxyacetyl)(4-{[(4-phenoxybenzyl)amino]carbonyl}-benzyl)amino]benzoic acid

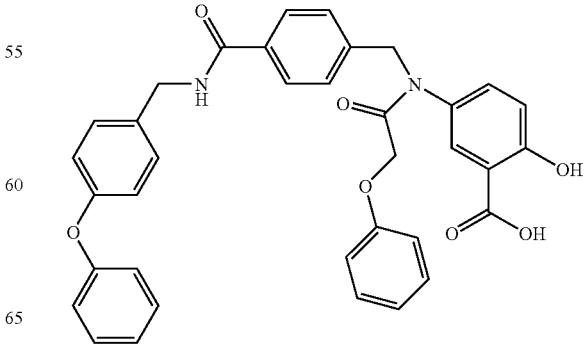

The title compound was prepared following the procedure A using 4-phenoxybenzylamine, 4-(chloromethyl)benzoyl chloride, phenoxyacetyl chloride and 6-amino-2,2-dimethyl-4H-1,3-benzodioxin-4-one. M⁺(ESI): 603.1

Example 15

2-hydroxy-5-{(4-{[(4-phenoxybenzyl)amino]carbonyl}benzyl)[4-(trifluoromethyl)benzoyl]amino}benzoic acid

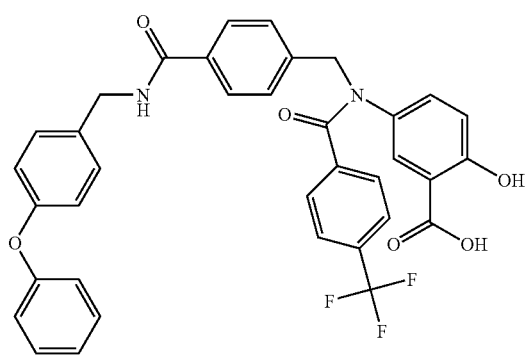

The title compound was prepared following the procedure A using 4-phenoxybenzylamine, 4-(chloromethyl)benzoyl chloride, 4-(trifluoromethyl)benzoyl chloride and 6-amino-2,2-dimethyl-4H-1,3-benzodioxin-4-one. M⁺(ESI): 641.0

Example 16

2-hydroxy-5-{(4-{[(4-phenoxybenzyl)amino]carbonyl}benzyl[(2E)-3-phenylprop-2-enoyl]amino}benzoic acid

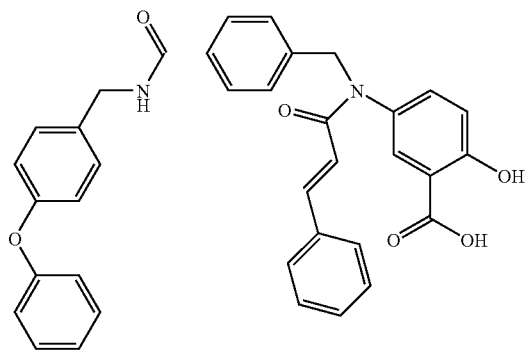

The title compound was prepared following the procedure A using 4-phenoxybenzylamine, 4-(chloromethyl)benzoyl chloride, (2E)-3-phenylacryloyl chloride and 6-amino-2,2-dimethyl-4H-1,3-benzodioxin-4-one. M⁺(ESI): 599.1

Example 17

5-[(N,N-dimethylglycyl)(4-{[(4-(phenoxybenzyl)amino]carbonyl}-benzyl)amino]-2-hydroxybenzoic acid

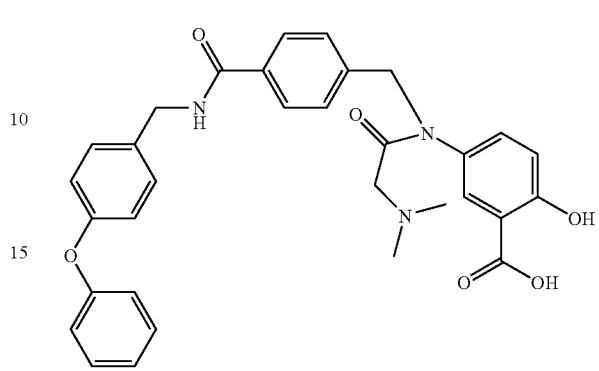

The title compound was prepared following the procedure A using 4-phenoxybenzylamine, 4-(chloromethyl)benzoyl chloride, N,N-dimethylglycyl chloride hydrochloride and 6-amino-2,2-dimethyl-4H-1,3-benzodioxin-4-one. M⁺(ESI): 554.2

Example 18

2-hydroxy-5-[(3-methylbut-2-enoyl)(4-{[(4-phenoxybenzyl)amino]carbonyl}benzyl)amino]benzoic acid

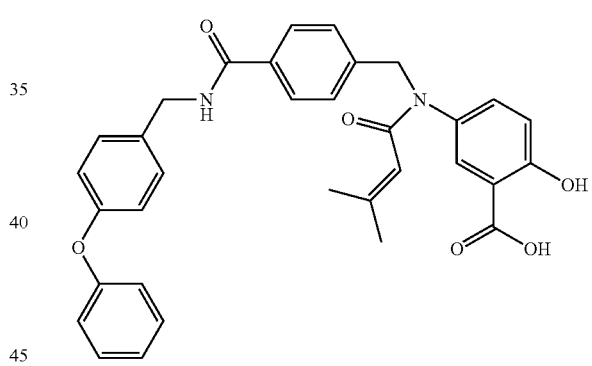

The title compound was prepared following the procedure A using 4-phenoxybenzylamine, 4-(chloromethyl)benzoyl chloride, 3-methylbut-2-enoyl chloride and 6-amino-2,2-dimethyl-4H-1,3-benzodioxin-4-one. M⁺(ESI): 551.1

Example 19

2-hydroxy-5-{[{4-[(octylamino)carbonyl]benzyl}(phenoxyacetyl)amino]-methyl}benzoic acid

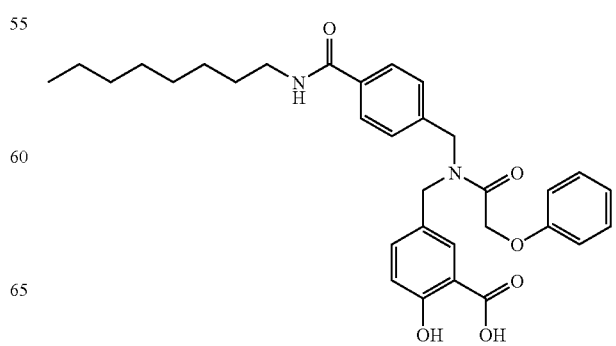

The title compound was prepared following the procedure A using octylamine, 4-(chloromethyl)benzoyl chloride, phenoxyacetyl chloride and 6-(aminomethyl)-2,2-dimethyl-4H-1,3-benzodioxin-4-one acetate. M+(ESI): 547.5

Example 20
2-hydroxy-5-({{4-[(octylamino)carbonyl]benzyl}[4-(trifluoromethyl)benzoyl]amino}methyl)benzoic acid

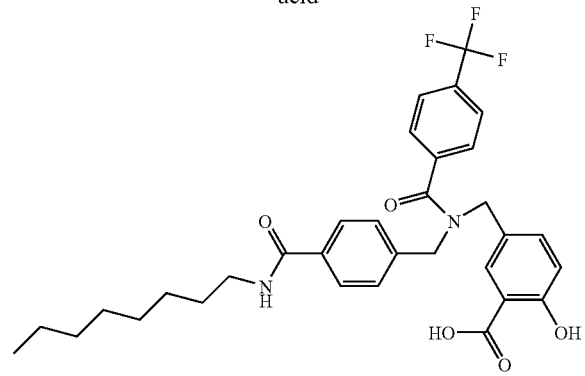

The title compound was prepared following the procedure A using octylamine, 4-(chloromethyl)benzoyl chloride, 4-(trifluoromethyl)benzoyl chloride and 6-(aminomethyl)-2,2-dimethyl-4H-1,3-benzodioxin-4-one acetate. M+(ESI): 585.4

Example 21
2-hydroxy-5-({{4-[(octylamino)carbonyl]benzyl}[(2E)-3-phenylprop-2-enoyl]amino}methyl)benzoic acid

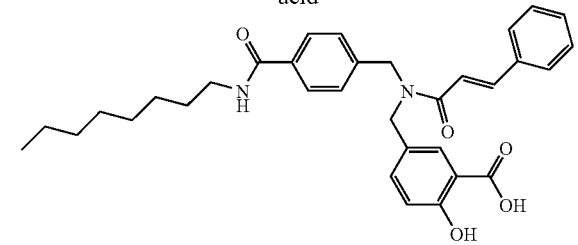

The title compound was prepared following the procedure A using octylamine, 4-(chloromethyl)benzoyl chloride, (2E)-3-phenylacryloyl chloride and 6-(aminomethyl)-2,2-dimethyl-4H-1,3-benzodioxin-4-one acetate. M+(ESI): 543.5

Example 22
5-{[(3-cyclopentylpropanoyl)(4-{[(4-pentylbenzyl)amino]carbonyl}benzyl)amino]methyl}-2-hydroxybenzoic acid

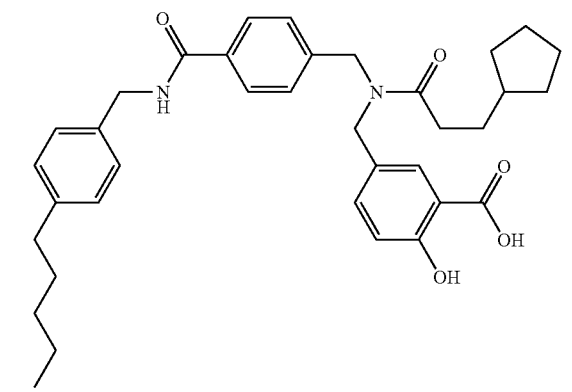

The title compound was prepared following the procedure A using 4-pentylbenzylamine, 4-(chloromethyl)benzoyl chloride, 3-cyclopentylpropanoyl chloride and 6-(aminomethyl)-2,2-dimethyl-4H-1,3-benzodioxin-4-one acetate. M+(ESI): 585.5

Example 23
2-hydroxy-5-{[(4-{[(4-pentylbenzyl)amino]carbonyl}benzyl)(phenoxyacetyl)amino]methyl}benzoic acid

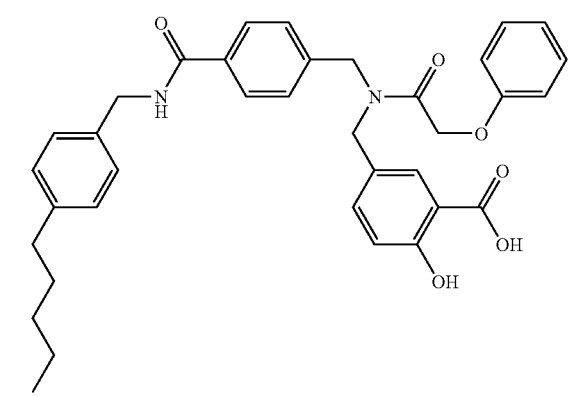

The title compound was prepared following the procedure A using 4-pentylbenzylamine, 4-(chloromethyl)benzoyl chloride, phenoxyacetyl chloride and 6-(aminomethyl)-2,2-dimethyl-4H-1,3-benzodioxin-4-one acetate. M+(ESI): 595.5

Example 24
2-hydroxy-5-({(4-{[(4-pentylbenzyl)amino]carbonyl}benzyl)[4-(trifluoromethyl)benzoyl]amino}methyl)benzoic acid

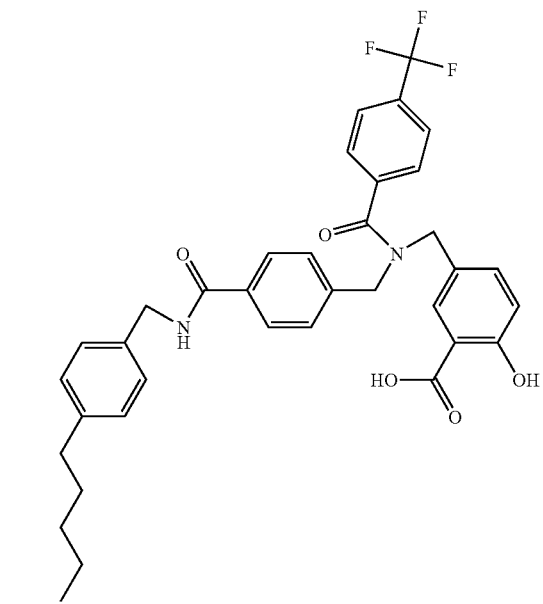

The title compound was prepared following the procedure A using 4-pentylbenzylamine, 4-(chloromethyl)benzoyl chloride, 4-(trifluoromethyl)benzoyl chloride and 6-(aminomethyl)-2,2-dimethyl-4H-1,3-benzodioxin-4-one acetate. M⁺(ESI): 633.4

Example 25

2-hydroxy-5-{[(3-methylbut-2-enoyl)(4-{[(4-pentyl-benzyl)amino]carbonyl}-benzyl)amino]methyl}benzoic acid

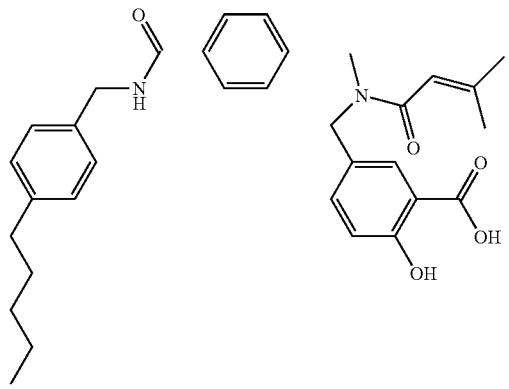

The title compound was prepared following the procedure A using 4-pentylbenzylamine, 4-(chloromethyl)benzoyl chloride, 3-methylbut-2-enoyl chloride and 6-(aminomethyl)-2,2-dimethyl-4H-1,3-benzodioxin-4-one acetate. M⁺(ESI): 543.5

Example 26

5-{[(3-cyclopentylpropanoyl)(4-{[(4-phenylbutyl)amino]carbonyl}benzyl)amino]methyl}-2-hydroxybenzoic acid

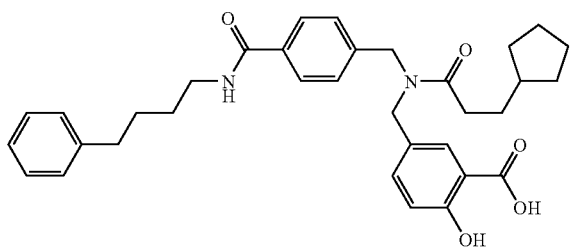

The title compound was prepared following the procedure A using 4-phenylbutylamine, 4-(chloromethyl)benzoyl chloride, 3-cyclopentylpropanoyl chloride and 6-(aminomethyl)-2,2-dimethyl-4H-1,3-benzodioxin-4-one acetate. M⁺(ESI): 557.5

Example 27

2-hydroxy-5-({[(4-{[(4-pentylbenzyl)amino]carbonyl}-1,3-thiazol-2-yl)methyl][(2E)-3-phenylprop-2-enoyl]amino}methyl)benzoic acid

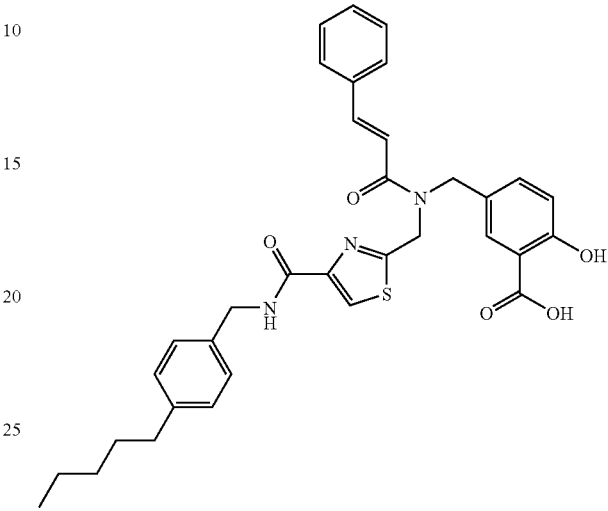

The title compound was prepared following the procedure A using 4-pentylbenzylamine, 2-(chloromethyl)-1,3-thiazole-4-carbonyl chloride, (2E)-3-phenylacryloyl chloride and 6-(aminomethyl)-2,2-dimethyl-4H-1,3-benzodioxin-4-one acetate. M⁺(ESI): 598.4

Example 28

[4-({(4-{[(4-phenoxybenzyl)amino]carbonyl}benzyl)[4-(trifluoromethyl)benzoyl]amino}methyl) phenoxy]acetic acid

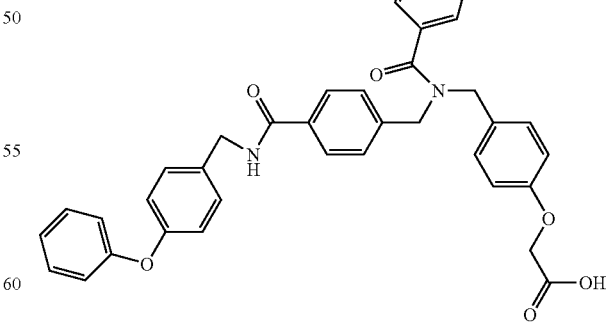

The title compound was prepared following the procedure A using 4-phenoxybenzylamine, 4-(chloromethyl)benzoyl chloride, 4-(trifluoromethyl)benzoyl chloride and methyl[4-(aminomethyl)phenoxy]acetate, acetate salt. M⁺(ESI): 669.2

Example 29
2-hydroxy-5-[(4-{[(4-pentylbenzyl)amino]carbonyl}benzyl)(3-phenylpropanoyl)amino]benzoic acid

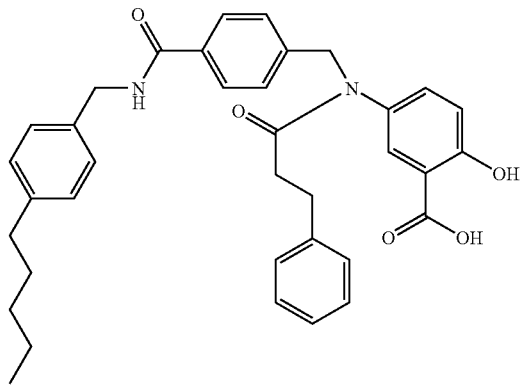

The title compound was prepared following the procedure A using 4-pentylbenzylamine, 4-(chloromethyl)benzoyl chloride, 3-phenylpropanoyl chloride and 6-amino-2,2-dimethyl-4H-1,3-benzodioxin-4-one. M$^+$(ESI): 579.4

Example 30
4-[(3-cyclopentylpropanoyl)(4-({[(4-pentylbenzyl)amino]carbonyl}-benzyl)amino]-2-hydroxybenzoic acid

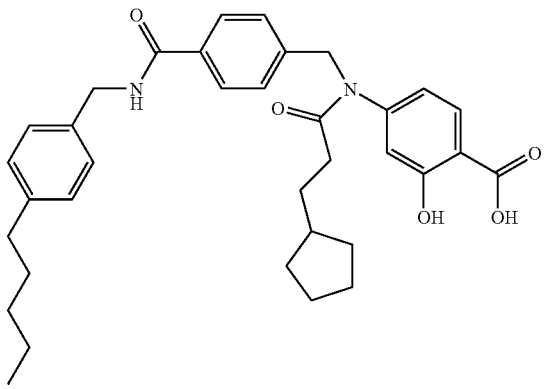

The title compound was prepared following the procedure A using 4-pentylbenzylamine, 4-(chloromethyl)benzoyl chloride, 3-cyclopentylpropanoyl chloride and 7-amino-2,2-dimethyl-4H-1,3-benzodioxin-4-one. M$^+$(ESI): 571.3

Example 31
2-hydroxy-4-{(4-{[(4-pentylbenzyl)amino]carbonyl}benzyl)[4-(trifluoromethyl)benzoyl]amino}benzoic acid

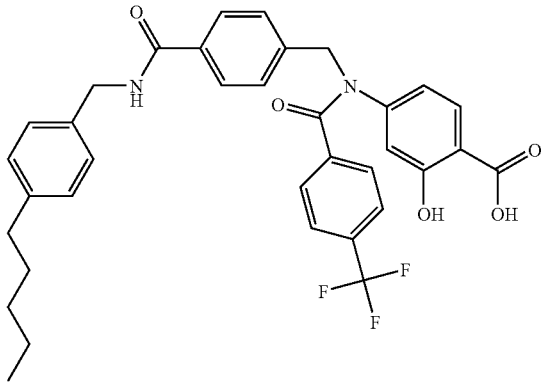

The title compound was prepared following the procedure A using 4-pentylbenzylamine, 4-(chloromethyl)benzoyl chloride, 4-(trifluoromethyl)benzoyl chloride and 7-amino-2,2-dimethyl-4H-1,3-benzodioxin-4-one. M$^+$(ESI): 619.3

Example 32
2-hydroxy-5-[{[2-(4-{[(4-pentylbenzyl)amino]carbonyl}phenyl)-1,3-thiazol-4-yl]methyl}(phenoxyacetyl)amino]benzoic acid

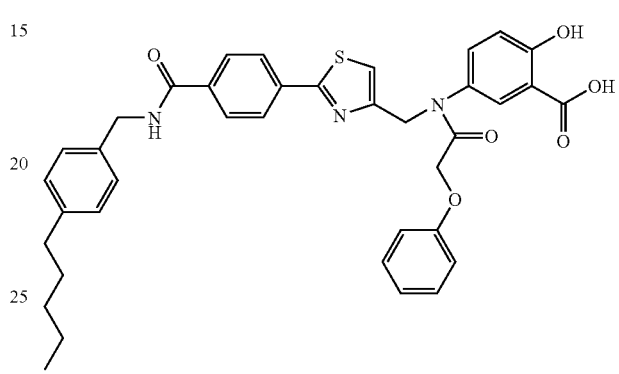

The title compound was prepared following the procedure A using 4-pentylbenzylamine, 4-[4-(chloromethyl)-1,3-thiazol-2-yl]benzoyl chloride, phenoxyacetyl chloride and 6-amino-2,2-dimethyl-4H-1,3-benzodioxin-4-one. M$^+$(ESI): 664.2

Example 33
2-hydroxy-5-{{[2-(4-{[(4-pentylbenzyl)amino]carbonyl}phenyl)-1,3-thiazol-4-yl]methyl}[4-(triflu

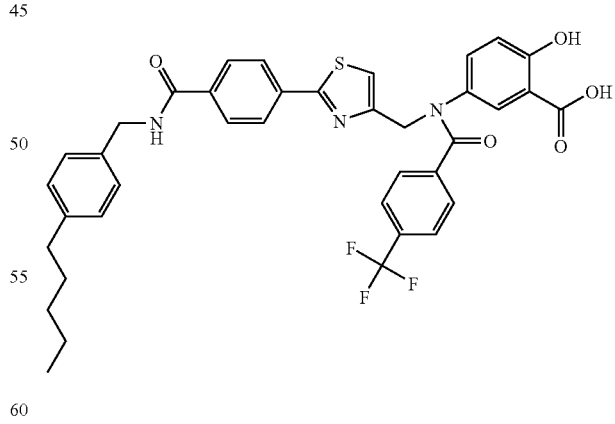

The title compound was prepared following the procedure A using 4-pentylbenzylamine, 4-[4-(chloromethyl)-1,3-thiazol-2-yl]benzoyl chloride, 4-(trifluoromethyl)benzoyl chloride and 6-amino-2,2-dimethyl-4H-1,3-benzodioxin-4-one. M$^+$(ESI): 702.2

Example 34

5-([(6-chloropyridin-3-yl)carbonyl]{[2-(4-{[(4-pentylbenzyl)amino]-carbonyl}phenyl)-1,3-thiazol-4-yl[9 methyl}amino)-2-hydroxybenzoic acid

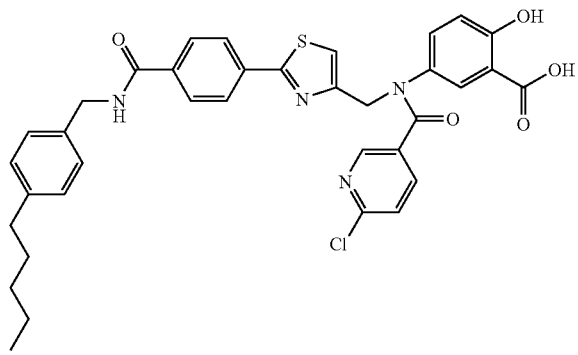

The title compound was prepared following the procedure A using 4-pentylbenzylamine, 4-[4-(chloromethyl)-1,3-thiazol-2-yl]benzoyl chloride, 6-chloronicotinoyl chloride and 6-amino-2,2-dimethyl-4H-1,3-benzodioxin-4-one.
$M^+(ESI)$: 669.2

Example 35

5-((4-cyanobenzyl){2-(4-{[(4-pentylbenzyl)amino]carbonyl}phenyl)-1,3-thiazol-4-yl]methyl}amino)-2-hydroxybenzoic acid

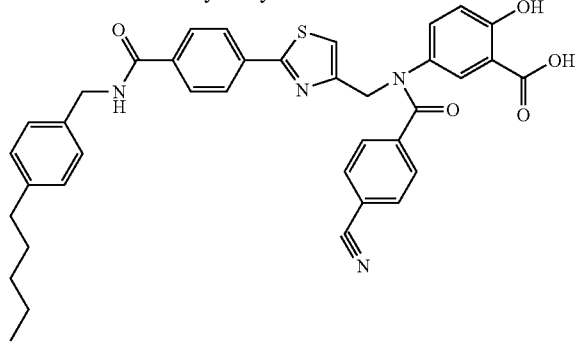

The title compound was prepared following the procedure A using 4-pentylbenzylamine, 4-[4-(chloromethyl)-1,3-thiazol-2-yl]benzoyl chloride, 4-cyanobenzoyl chloride and 6-amino-2,2-dimethyl-4H-1,3-benzodioxin-4-one.
$M^+(ESI)$: 659.2

Example 36

2-hydroxy-5-((3-methylbut-2-enoyl){[2-(4-{[(4-pentylbenzyl)amino]-carbonyl}phenyl)-1,3-thiazol-4-yl]methyl}amino)benzoic acid

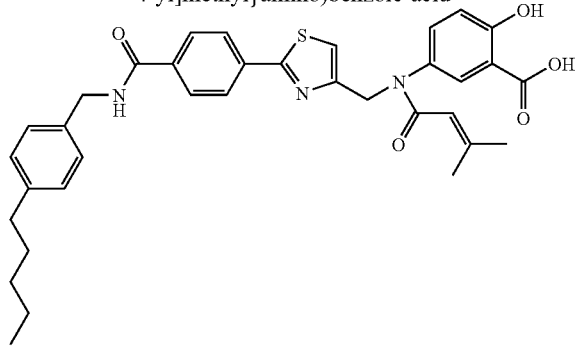

The title compound was prepared following the procedure A using 4-pentylbenzylamine, 4-[4-(chloromethyl)-1,3-thiazol-2-yl]benzoyl chloride, 3-methylbut-2-enoyl chloride and 6-amino-2,2-dimethyl-4H-1,3-benzodioxin-4-one.
$M^+(ESI)$: 612.3

Example 37

5-((3-cyclopentylpropanoyl){[2-(4-{[(4-phenoxybenzyl)amino]-carbonyl}phenyl)-1,3-thiazol-4-yl]methyl}amino)-2-hydroxybenzoic acid

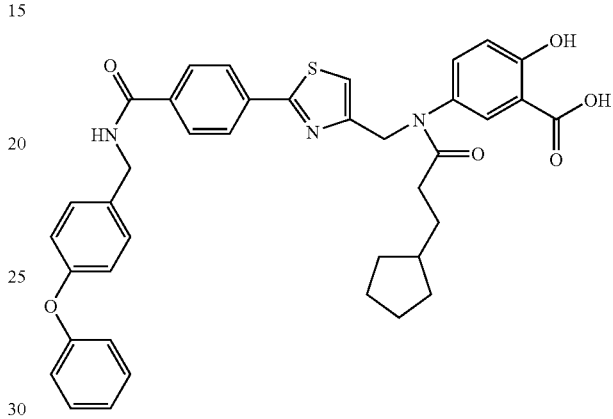

The title compound was prepared following the procedure A using 4-phenoxybenzylamine, 4-[4-(chloromethyl)-1,3-thiazol-2-yl]benzoyl chloride, 3-cyclopentylpropanoyl chloride and 6-amino-2,2-dimethyl-4H-1,3-benzodioxin-4-one.
$M^+ESI)$: 676.3

Example 38

2-hydroxy-5-{{[2-(4-{[(4-phenoxybenzyl)amino]carbonyl}phenyl)-1,3-thiazol-4-yl]methyl}[4-(trifluoromethyl)benzoyl]amino}benzoic acid

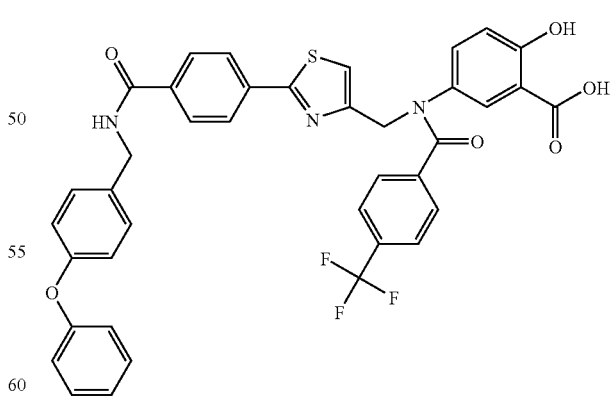

The title compound was prepared following the procedure A using 4-phenoxybenzylamine, 4-[4-(chloromethyl)-1,3-thiazol-2-yl]benzoyl chloride, 4-(trifluoromethyl)benzoyl chloride and 6-amino-2,2-dimethyl-4H-1,3-benzodioxin-4-one. $M^+(ESI)$: 724.1

Example 39

2-hydroxy-5-[{[2-(4-{[(4-phenoxybenzyl)amino]carbonyl}phenyl-1,3-thiazol-4-yl]methyl}(3-phenyl-propanoyl)amino]benzoic acid

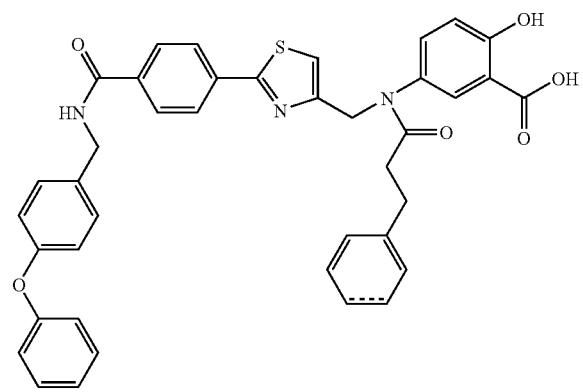

The title compound was prepared following the procedure A using 4-phenoxybenzylamine, 4-[4-(chloromethyl)-1,3-thiazol-2-yl]benzoyl chloride, 3-phenylpropanoyl chloride and 6-amino-2,2-dimethyl-4H-1,3-benzodioxin-4-one. M$^+$(ESI): 684.2

Example 40

5-(benzoyl{[2-(4-{[(4-phenoxybenzyl)amino]carbonyl}phenyl)-1,3-thiazol-4-yl]methyl}amino)-2-hydroxybenzoic acid

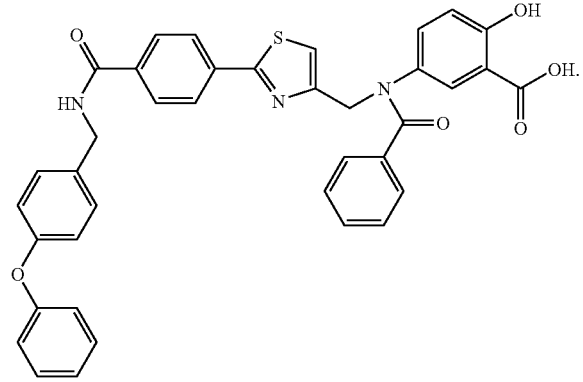

The title compound was prepared following the procedure A using 4-phenoxybenzylamine, 4-[4-(chloromethyl)-1,3-thiazol-2-yl]benzoyl chloride, benzoyl chloride and 6-amino-2,2-dimethyl-4H-1,3-benzodioxin-4-one. M$^+$(ESI): 656.2

Example 41

[4-({{[2-(4-{[(4-pentylbenzyl)amino]carbonyl}phenyl)-1,3-thiazol-4-yl]methyl}[4-(trifluoromethyl)benzoyl]amino}methyl)phenoxy]acetic acid

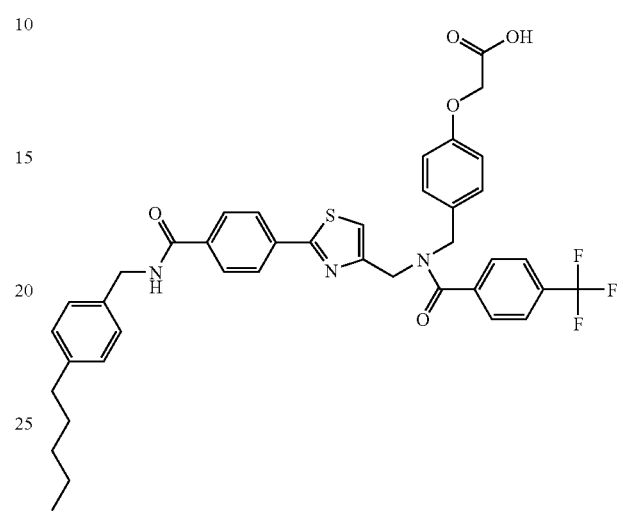

The title compound was prepared following the procedure A using 4-pentylbenzylamine, 4-[4-(chloromethyl)-1,3-thiazol-2-yl]benzoyl chloride, 4-(trifluoromethyl)benzoyl chloride and methyl[4-(aminomethyl)phenoxy]acetate, acetate salt. M$^+$(ESI): 730

Example 42

(4-{[{[2-(4-{[(4-pentylbenzyl)amino]carbonyl}phenyl)-1,3-thiazol-4-yl]methyl}(3-phenylpropanoyl)amino]methyl}phenoxy)acetic acid

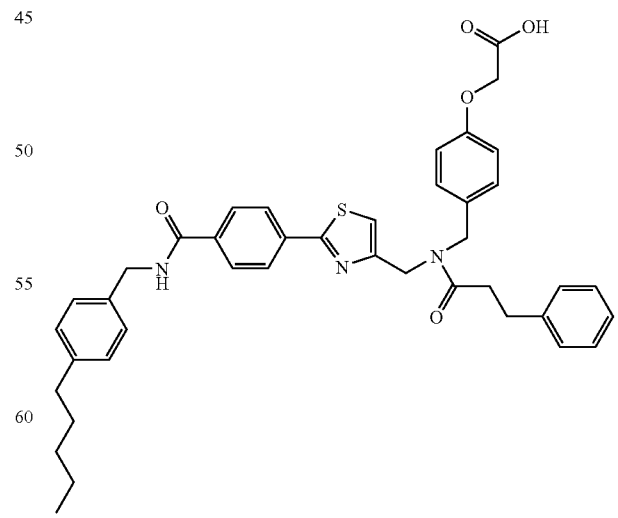

The title compound was prepared following the procedure A using 4-pentylbenzylamine, 4-[4-(chloromethyl)-1,3-thiazol-2-yl]benzoyl chloride, 3-phenylpropanoyl chloride and methyl[4-(aminomethyl)phenoxy]acetate, acetate salt. M⁺(ESI): 690.2

Example 43

[4-({{[2-(4-{[(4-phenylbutyl)amino]carbonyl}phenyl)-1,3-thiazol-4-yl]methyl}[4-(trifluoromethyl)benzoyl]amino}methyl)phenoxy]acetic acid

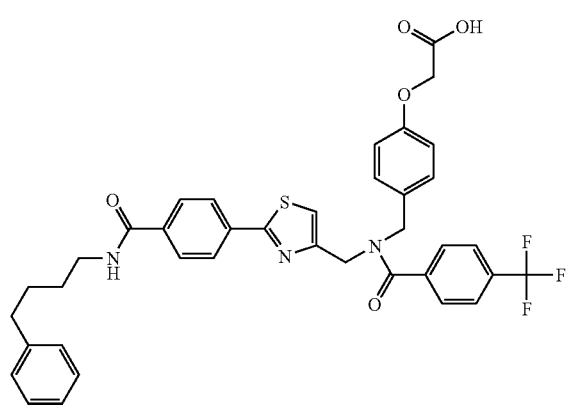

The title compound was prepared following the procedure A using 4-phenylbutylamine, 4-[4-(chloromethyl)-1,3-thiazol-2-yl]benzoyl chloride, 4-(trifluoromethyl)benzoyl chloride and methyl[4-(aminomethyl)phenoxy]acetate, acetate salt. M⁺(ESI): 702

Example 44

(4-{[{[2-(4-{[(4-phenylbutyl)amino]carbonyl}phenyl)-1,3-thiazol-4-yl]methyl}(3-phenylpropanoyl)amino]methyl}phenoxy)acetic acid

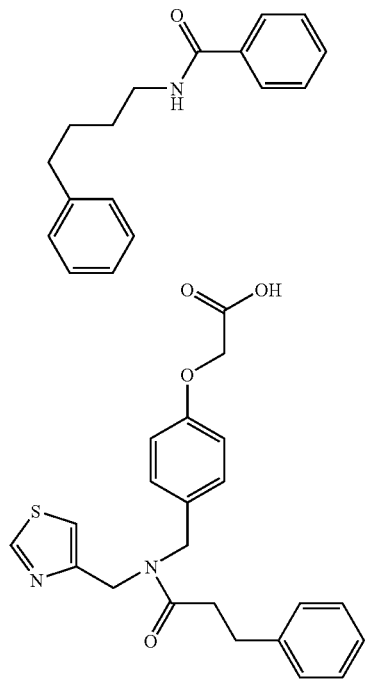

The title compound was prepared following the procedure A using 4-phenylbutylamine, 4-[4-(chloromethyl)-1,3-thiazol-2-yl]benzoyl chloride, 3-phenylpropanoyl chloride and methyl[4-(aminomethyl)phenoxy]acetate, acetate salt. M⁺(ESI): 662.1

Example 45

[4-({{[2-(4-{[(4-phenylbutyl)amino]carbonyl}phenyl)-1,3-thiazol-4-yl]methyl}[(2E)-3-phenylprop-2-enoyl]amino}methyl)phenoxy]acetic acid

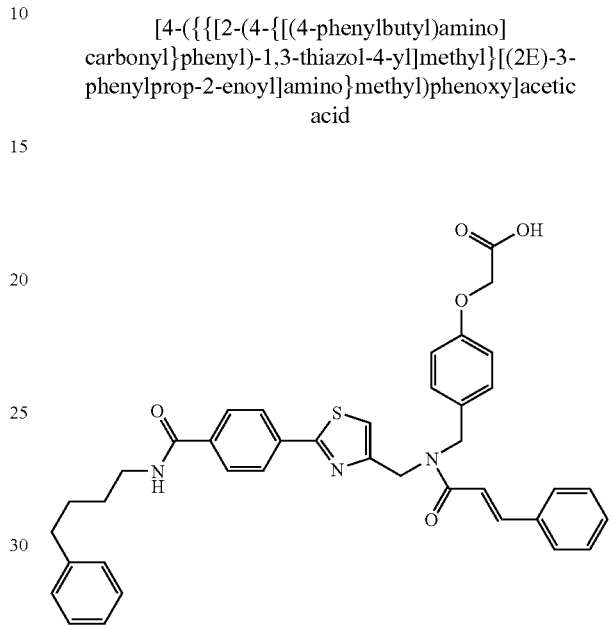

The title compound was prepared following the procedure A using 4-phenylbutylamine, 4-[4-(chloromethyl)-1,3-thiazol-2-yl]benzoyl chloride, (2E)-3-phenylacryloyl chloride and methyl[4-(aminomethyl)phenoxy]acetate, acetate salt. M⁺(ESI): 660.1

Example 46

{4-[((N,N-dimethylglycyl){[2-(4-{[(4-phenylbutyl)amino]carbonyl}phenyl)-1,3-thiazol-4-yl]methyl}amino)methyl]phenoxy}acetic acid

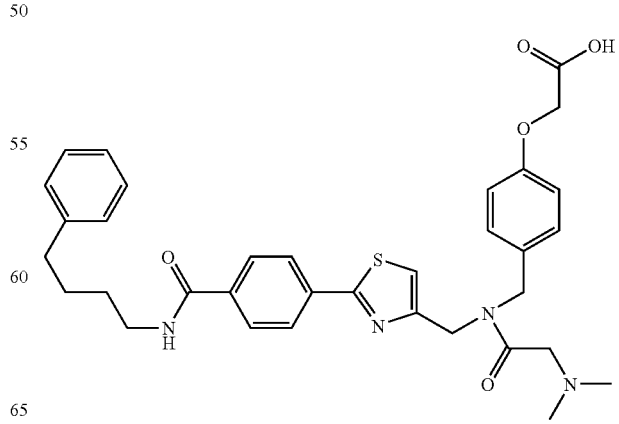

The title compound was prepared following the procedure [79 [0 using 4-phenylbutylamine, 4-[4-(chloromethyl)-1,3-thiazol-2-yl]benzoyl chloride, N,N-dimethylglycyl chloride hydrochloride and methyl[4-(aminomethyl)phenoxy]acetate, acetate salt. M⁺(ESI): 615.2

Example 47

{4-[((cyclohexylcarbonyl){[2-(4-{[(4-phenylbutyl)amino]carbonyl}phenyl)-1,3-thiazol-4-yl]methyl}amino)methyl]phenoxy}acetic acid

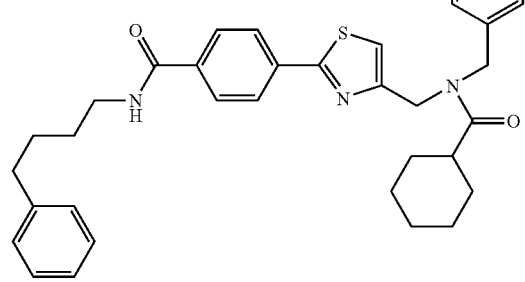

The title compound was prepared following the procedure A using 4-phenylbutylamine, 4-[4-(chloromethyl)-1,3-thiazol-2-yl]benzoyl chloride, cyclohexanecarbonyl chloride and methyl[4-(aminomethyl)phenoxy]acetate, acetate salt. M⁺(ESI): 640.2

Example 48

{4-[((phenoxyacetyl){[2-(4-{[(4-phenoxybenzyl)amino]carbonyl}phenyl)-1,3-thiazol-4-yl]methyl}amino)methyl]phenoxy}acetic acid

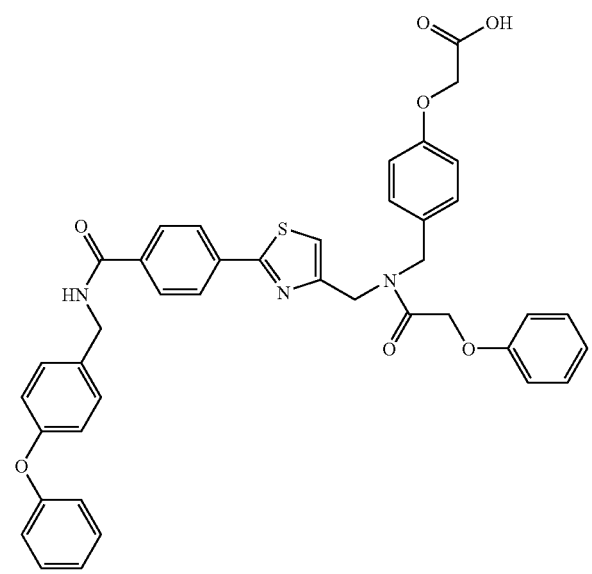

The title compound was prepared following the procedure A using 4-phenoxybenzylamine, 4-[4-(chloromethyl)-1,3-thiazol-2-yl]benzoyl chloride, phenoxyacetyl chloride and methyl[4-(aminomethyl)phenoxy]acetate, acetate salt. M⁺(ESI): 714

Example 49

[4-({{[2-(4-{[(4-phenoxybenzyl)amino]carbonyl}phenyl)-1,3-thiazol-4-yl]methyl}[4-(trifluoromethyl)benzoyl]amino}methyl)phenoxy]acetic acid

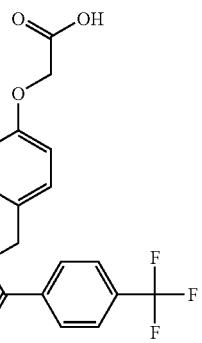

The title compound was prepared following the procedure A using 4-phenoxybenzylamine, 4-[4-(chloromethyl)-1,3-thiazol-2-yl]benzoyl chloride, 4-(trifluoromethyl)benzoyl chloride and methyl[4-(aminomethyl)phenoxy]acetate, acetate salt. M$^+$(ESI): 752.9

Example 50

(4-{[{[2-(4-{[(4-phenoxybenzyl)amino]carbonyl}phenyl)-1,3-thiazol-4-yl]methyl}(3-phenylpropanoyl)amino]methyl}phenoxy)acetic acid

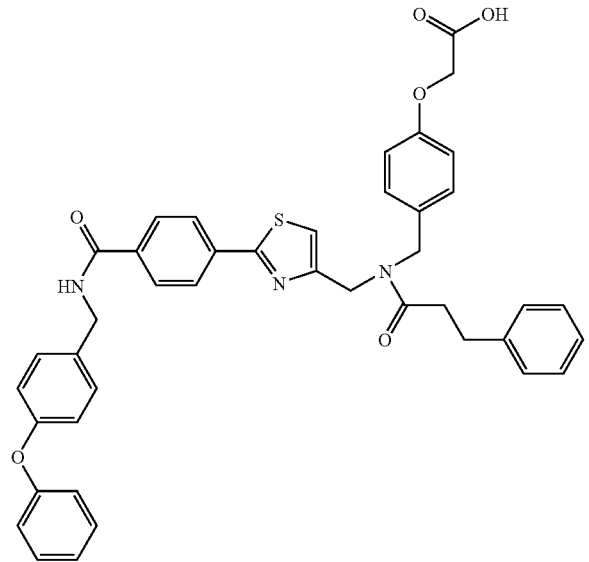

The title compound was prepared following the procedure A using 4-phenoxybenzylamine, 4-[4-(chloromethyl)-1,3-thiazol-2-yl]benzoyl chloride, 3-phenylpropanoyl chloride and methyl[4-(aminomethyl)phenoxy]acetate, acetate salt. M$^+$(ESI): 712.1

Example 51

{4-[((cyclohexylcarbonyl){[2-(4-{[(4-phenoxybenzyl)amino]carbonyl}-phenyl)-1,3-thiazol-4-yl]methyl}amino)methyl]phenoxy}acetic acid

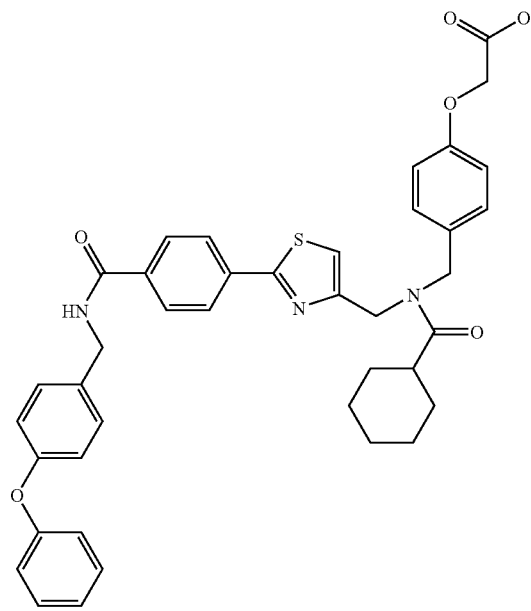

The title compound was prepared following the procedure A using 4-phenoxybenzylamine, 4-[4-(chloromethyl)-1,3-thiazol-2-yl]benzoyl chloride, cyclohexanecarbonyl chloride and methyl[4-(aminomethyl)phenoxy]acetate, acetate salt. M$^+$(ESI): 690.2

Example 52

[4-({[(2-{4-[(octylamino)carbonyl]phenyl}-1,3-thiazol-4-yl)methyl][4-(trifluoromethyl)benzoyl]amino}methyl)phenoxy]acetic acid

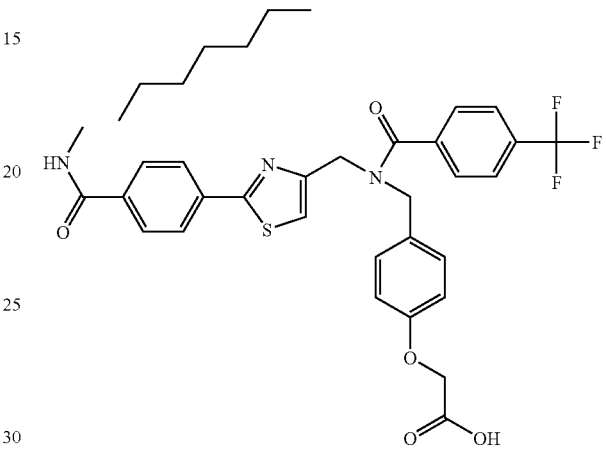

The title compound was prepared following the procedure A using octylamine, 4-[4-(chloromethyl)-1,3-thiazol-2-yl]benzoyl chloride, 4-(trifluoromethyl)benzoyl chloride and methyl[4-(aminomethyl)phenoxy]acetate, acetate salt. M$^+$(ESI): 682.1

Example 53

(4-{[[(2-{4-[(octylamino)carbonyl]phenyl}-1,3-thiazol-4-yl)methyl](3-phenylpropanoyl)amino]methyl}phenoxy)acetic acid

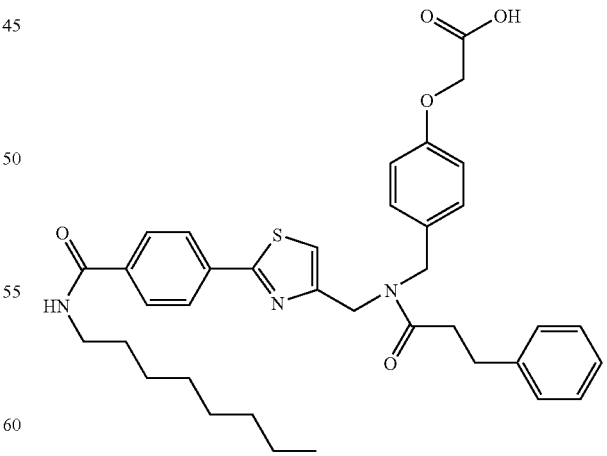

The title compound was prepared following the procedure A using octylamine, 4-[4 (chloromethyl)-1,3-thiazol-2-yl]benzoyl chloride, 3-phenylpropanoyl chloride and methyl [4-(aminomethyl)phenoxy]acetate, acetate salt. M$^+$(ESI): 642.2

Example 54

Preparation of a Pharmaceutical Formulation

Formulation 1—Tablets

An aryl dicarboxamide of formula (I) is admixed as a dry powder with a dry gelatin binder in an approximate 1:2 weight ration. A minor amount of magnesium stearate is added as a lubricant. The mixture is formed into 240-270 mg tablets (80-90 mg of active piperazine-2-carboxamide compound per tablet) in a tablet press.

Formulation 2—Capsules

An aryl dicarboxamide of formula (I) is admixed as a dry powder with a starch diluent in an approximate 1:1 weight ratio. The mixture is filled into 250 mg capsules (125 mg of active piperazine-2-carboxamide compound per capsule).

Formulation 3—Liquid

An aryl dicarboxamide of formula (I), sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.

Formulation 4—Tablets

An aryl dicarboxamide of formula (I), is admixed as a dry powder with a dry gelatin binder in an approximate 1:2 weight ratio. A minor amount of magnesium stearate is added as a lubricant. The mixture is formed into 300-600 mg tablets (150-300 mg of active aryl dicarboxamide derivative) in a tablet press.

Formulation 5—Injection

An aryl dicarboxamide of formula (I), is dissolved in a buffered sterile saline injectable aqueous medium to a concentration of approximately 5 mg/ml.

Example 55

Biological Assays

The compounds of formula (I), may be subjected to the following assays:
(1) The PTP Enzyme Assay
(2) The in vivo assay in db/db mice (1) The PTP Enzyme Assay (In Vitro Assay)

Assays for the determination of the PTP inhibitory activity of test compounds are well known to a person skilled in the art. An example of such an assay is described below:

The PTP Enzyme Assay aims at determining the extent of inhibition of PTPs, e.g. of PTP1B, SHP-1, SHP-2, or GLEPP-1 in the presence of a test compound of formula (I). The inhibition is illustrated by $IC_{50}$ values which denote the concentration of test compound necessary to achieve an inhibition of 50% of said PTP's using the following concentration of the PTP substrate DiFMUP:

5 µM DiFMUP for PTP1B;
20 µM DiFMUP for SHP-1 and SHP-2;
30 µM DiFMUP for GLEPP-1.

a) PTPs Cloning

The cloning and expression of the catalytic domain e.g. of PTP1B, may be performed as described in *J. Biol. Chem.* 2000, 275(13), pp 9792-9796.

b) Materials and Methods

The DiFMUP assay allows to follow the dephosphorylation of DiFMUP (6,8-DiFluoro-4-MethylUmbelliferyl Phosphate)—which is the PTP substrate—mediated by PTP into its stable hydrolysis product, i.e. DiFMU (6,8-difluoro-7-hydroxy coumarin). Due to its rather low pKa and its high quantum yield, DiFMU allows to measure both acidic and alkaline phosphatase activities with a great sensitivity.

Assays were performed in a 96 well plate format, using the catalytic core of a human recombinant PTP as the enzyme and 6,8-DiFluoro-4-MethylUmbelliferyl Phosphate (DiFMUP, Molecular Probes, D-6567) as a substrate. Compounds to be tested were dissolved in 100% DMSO at a concentration of 2 mM. Subsequent dilutions of the test compounds (to yield a concentration of 100, 30, 10, 3, 1, 0.3, 0.1, 0.03, 0.01, 0.001 µM) were performed in 60% DMSO manually. 8 µl of diluted compound or vehicle (60% DMSO=control) was distributed to a black Costar 96 well plate. 42 µl of human recombinant PTP enzyme diluted in assay buffer (20 mM Tris HCl pH 7.5, 0.01% IGEPAL CA-630, 0.1 mM ethylenediaminetetracetic acid, 1 mM DL-Dithiothreitol) can be added to the dilutions of compound or vehicle (distributed to a black Costar 96 well plate), followed by 50 µl of DiFMUP diluted in the assay buffer. The reaction ran for 30 minutes at room temperature before reading the fluorescence intensity (integral or intensity) on a Perkin-Elmer Victor 2 spectrofluorimeter (excitation of 6,8-difluoro-7-hydroxy coumarin is at 355 nm, the emission at 460 nm, for 0.1 s). The percentage of inhibition is determined by measuring the relative fluorescence ion absence of a test compound (PTP inhibitor), i.e. with the solvent alone (5% DMSO). The $IC_{50}$ values for inhibition were determined in triplicates.

The tested compounds according to formula (I) display an inhibition (illustrated by $IC_{50}$ values) with regard to PTP of preferably less than 20 µM, more preferred less than 5 µM.

For instance, the compound of example 1 displays an $IC_{50}$ value of 1.0 µM in respect of PTP1B, an $IC_{50}$ value of 1.2 µM in respect of GLEPP-1, an $IC_{50}$ value of 4.0 and 1.9 µM in respect of SHP-1 and SHP-2.

(2) In Vivo Assay in db/db Mice

The compounds may be subjected to the following assay which aims at determining the anti-diabetic effect of the test compounds of formula (I) in a model of postprandial glycemia in db/db mice, in vivo.

The assay is performed as follows:

A total of 24 db/db mice (about 8-9 weeks; obtained from IFFACREDO, l'Arbreste, France) are fasted during 20 hours.

4 groups, each consisting of 6 animals are formed:
Group 1: The animals are administered (per os) a dose of 10 mg/kg of vehicle.
Group 2: The animals are administered (per os) a dose of 20 mg/kg of the test compound according to formula (I).
Group 3: The animals are administered (per os) a dose of 100 mg/kg of the test compound according to formula (I).
Group 4: The animals are administered (per os) a dose of 200 mg/kg of the test compound according to formula (I).

After oral administration of the compounds of formula (I) solubilized or sus-pended in CarboxyMethylCellulose (0.5%), Tween 20 (0.25%) and water as vehicle, the animals have access to commercial food (D04, UAR, Villemoisson/Orge, France) ad libitum. The diabetic state of the mice is verified by determining the blood glucose level before drug administration. Blood glucose and serum insulin levels are then determined 4 hrs after drug administration.

The determination of the blood glucose level is performed using a glucometer (Precision Q.I.D., Medisense, Abbot, ref. 212.62.31).

The determination of the Insulin level is performed using an ELISA kit (Crystal CHEM, Ref. INSK R020).

Changes in blood glucose and serum insulin of drug treated mice is expressed as a percentage of control (group 1 represents the vehicle treated mice).

LIST OF REFERENCES

*American Journal of Medicine,* 60, 80 (1976) by Reaven et al;
*Metabolism,* 34, 7 (1985) by Stout et al.;
*Diabetes/Metabolism Reviews,* 5, 547 (1989) by Pyorala et al;
*European Journal of Endocrinology* 138,269-274 (1998) by A. Dunaif;
*Endocrine Reviews* 18(6), 774-800 (1997);
*Diabetes Care,* 14, 173 (1991) by DeFronzo and Ferranninni;
*J. Mol. Med.* 78, 473-482 (2000) by A. Cheng et al.;
*Current Opinion in Drug Discovery & Development* 3(5), 527-540 (2000);
*Molecular and Cellular Biology,* 5479-5489 (2000) by Lori Klaman et al.;
*Diabetes,* 40, 939 (1991) by McGuire et al.;
*J. Clinical Invest.,* 84, 976 (1989) by Meyerovitch et al;
*Metabolism,* 44, 1074, (1995) by Sredy et al.;
*Curr. Opin. Chem. Biol.,* 5(4), 416-23 (2001) by Zhang et al.;
*J. Biol. Chem.,* 275(52), 41439-46 (2000) by Bjorge J. D et al.;
*J. Neurosci. Res.,* 63(2), 143-150 (2001) by Pathre et al.;
*Mol. Brain. Res.,* 28(1), 110-16 (1995) by Shock L. P et al;
*Biochemical Pharmacology,* Vol. 60, 877-883, (2000) by Brian P. Kennedy et al.;
*Annu. Rev. Physiol.* 62 p. 413-437 (2000) by Ahima R. S. et al;
*Developmental Cell.,* vol. 2, p. 497-503 (2002);
*Bioorganic Medicinal Chemistry Letters* 9(19) p. 2849-5, (1999) by G. Bergnes et al.
WO 03/024955

The invention claimed is:

1. A method of treating type II diabetes or obesity, comprising administering to a subject in need of such treatment an effective amount of at least one member selected from the group consisting of an aryl dicarboxamide of formula (Ia), formula (Ib), and formula (Ic):

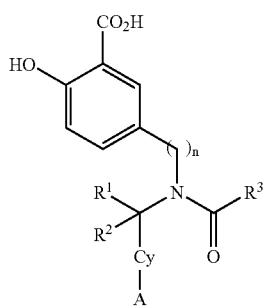
(Ia)

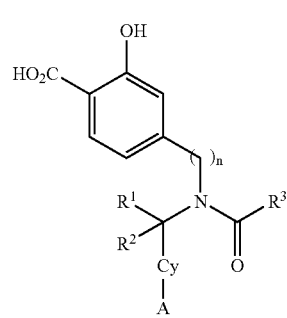
(Ib)

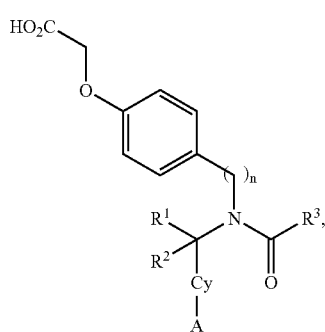
(Ic)

a geometrical isomer thereof, an optically active form thereof, and a pharmaceutically acceptable salt thereof, wherein:

A is an aminocarbonyl moiety of the formula—CO—NHR$^6$, wherein R$^6$ is a phenyl group attached directly or through an alkylene group, a phenyl-phenoxy group or an octyl group;

Cy is a phenyl group or a thiazole-phenyl group;

n is either 0 or 1;

R$^1$ and R$^2$ are hydrogen;

R$^3$ is selected from the group consisting of: (i) an alkyl group optionally substituted with an amino group, and (ii) a cyclopentyl group, a cyclohexyl group, a phenyl group, or a pyridyl group, attached directly or through an alkylene group or an oxo group, and optionally substituted with a cyano group or a fluoromethyl group.

2. An aryl dicarboxamide according to any of formulae (Ia), (Ib) or (Ic):

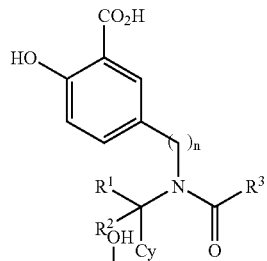
(Ia)

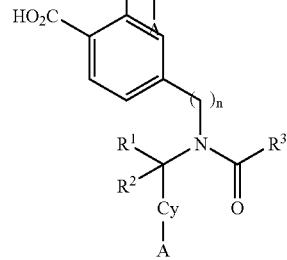
(Ib)

-continued

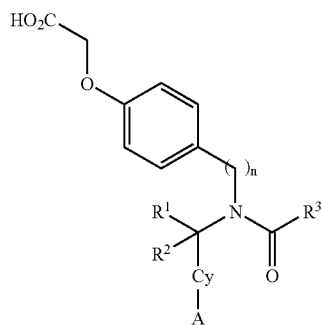

(Ic)

wherein

A is an aminocarbonyl moiety of the formula—CO—NHR⁶ wherein R⁶ is a phenyl group attached directly or through an alkylene group, a phenyl-phenoxy group, or an octyl group;

Cy is a phenyl group or a thiazole-phenyl group;

n is either 0 or 1;

$R^1$ and $R^2$ are hydrogen;

$R^3$ is selected from the group consisting of: (i) an alkyl group optionally substituted with an amino group, and (ii) a cyclopentyl group, a cyclohexyl group, a phenyl group, or a pyridyl group, attached directly or through an alkylene group or an oxo group, and optionally substituted with a cyano group or a fluoromethyl group.

3. An aryl dicarboxamide according to formula (Ib) or (Ic):

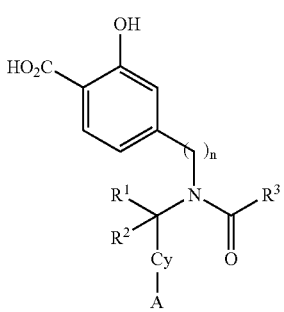

(Ib)

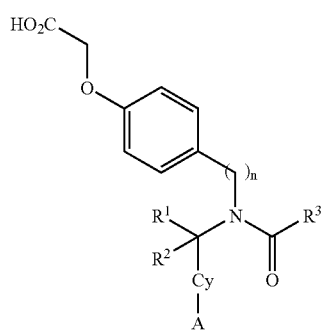

(Ic)

wherein

A is an aminocarbonyl moiety of the formula—CO—NHR⁶ wherein R⁶ a phenyl group attached directly or through an alkylene group, a phenyl-phenoxy group, or an octyl group;

Cy is a phenyl group or a thiazolyl-phenyl group;

n is either 0 or 1;

$R^1$ and $R^2$ are hydrogen;

$R^3$ is selected from the group consisting of:(i) an alkyl group optionally substituted with an amino group, and (ii) a cyclopentyl group, a cyclohexyl group, a phenyl group, or a pyridyl group, attached directly or through an alkylene group or an oxo group, and optionally substituted with a cyano group or a fluoromethyl group.

4. An aryl dicarboxamide selected from the group consisting of:

5-[(3-cyclopentylpropanoyl)(4-{[(4-phenoxybenzyl)amino]carbonyl}benzyl)amino]-2-hydroxybenzoic acid;

5[(3-cyclopentylpropanoyl)(4-{[(4-phenoxybenzyl)amino]carbonyl}benzyl)amino]-2-hydroxybenzoic acid;

[4-({{[2-(4-{[(4-pentylbenzyl)amino]carbonyl}phenyl)-1,3-thiazol-4-yl]methyl}-[(2E)-3-phenylprop-2-enoyl[amino}methyl)phenoxy]acetic acid;

5(3-cyclopentylpropanoyl)(4-{[(4-pentylbenzyl)amino]carbonyl}benzyl)amino]-2-hydroxybenzoic acid;

2-hydroxy-5-{(4-{[(4-pentylbenzyl)amino]carbonyl}benzyl)[4-(trifluoromcthyl)-benzoyl]amino}benzoic acid;

2-hydroxy-5[[(4-{[(4-phenoxybenzyl)amino]carbonyl}-1,3-thiazol-2-yl)methyl](3-phenylpropanoyl)amino]benzoic acid;

5-{benzoyl[(4-{[(4-phenoxybenzyl)amino]carbonyl}-1,3-thiazol-2-yl)methyl]-amino}-2-hydroxybenzoic acid;

2-hydroxy-5-{[(4-{[(4-phenoxybenzyl)amino]carbonyl}-1,3-thiazol-2-yl)methyl][-4-(trifluoromethyl)benzoyl]amino}benzoic acid;

5-[(cyclohexylcarbonyl)(4-{[(4-phenoxybcnzyl)amino]carbonyl}benzyl)amino]-2-hydroxybenzoic acid;

2-hydroxy-5-[(4-{[(4-phenoxybenzyl)amino]carbonyl}benzyl)(3-phenylpropanoyl)-amino]benzoic acid;

5-[benzoyl(4-{[(4-phenoxybenzyl)amino]carbonyl}benzyl)amino]-2-hydroxybenzoic acid;

5-[acetyl(4-{[(4-phenoxybenzyl)amino]carbonyl}benzyl)amino]-2-hydroxybenzoic acid;

5-[(4-cyanobenzoyl)(4-{[(4-phenoxybenzyl)amino]carbonyl}benzyl)amino]-2-hydroxybenzoic acid;

2-hydroxy-5-[(phenoxyacetyl)(4-{[4-phenoxybenzyl)amino]carbonyl}benzyl)-amino]-benzoic acid;

2-hydroxy-5-{(4-{[4-phenoxybenzyl)amino]carbonyl}benzyl)[4-(trifluoromethyl)-benzoyl]amino}benzoic acid;

2-hydroxy-5-{(4-{[(4-phenoxybenzyl)amino]carbonyl}benzyl)[(2E)-3-phenylprop-2-enoyl amino}benzoic acid;

5-[(N,N-dimethylglycyl)(4-{[(4-phenoxybenzyl)amino]carbonyl}benzyl)amino]-2-hydroxybenzoic acid;

2-hydroxy-5-[(3-methylbut-2-enoyl)(4-{[(4-phenoxybenzyl)amino]carbonyl}benzyl)-amino]benzoic acid;

2-hydroxy-5-{[{4-[(octylamino)carbonyl]benzyl}(phenoxyacetyl)amino]methyl}-benzoic acid;

2-hydroxy-5-({{4-[(octylamino)carbonyl]benzyl}[4-(trifluoromethyl)benzoyl]-amino}methyl)benzoic acid;

2-hydroxy-5-({{4-[(octylamino)carbonyl]benzyl}[(2E)-3-phenylprop-2-enoyl]-amino}methyl)benzoic acid;

5-{[(3-cyclopentylpropanoyl)(4-{[(4-pentylbenzyl)amino]carbonyl}benzyl)-amino]methyl}-2-hydroxybenzoic acid;

2-hydroxy-5-{[(4-{[(4-pentylbenzyl)amino]carbonyl}benzyl)(phenoxyacetyl)-amino]methyl}benzoic acid;

2-hydroxy-5-({(4-{[(4-pentylbenzyl)amino]carbonyl}benzyl)[4-(trifluoromethyl)-benzoyl]amino}methyl)benzoic acid;

2-hydroxy-5-{[(3-methylbut-2-enoyl)(4-{[(4-pentylbenzyl)amino]carbonyl}-benzyl)amino]methyl}benzoic acid;

5-{[(3-cyclopentylpropanoyl)(4-{[(4phenylbutyl)amino]carbonyl}benzyl)-amino]methyl}-2-hydroxybenzoic acid;

2-hydroxy-5-({[(4-{[(4-pentylbenzyl)amino]carbonyl}-1,3-thiazol-2-yl)methyl][(2E)-3-phenylprop-2-enoyl]amino}methyl)benzoic acid;

[4-({(4-{[(4-phenoxybenzyl)amino]carbonyl}benzyl)[4trifluoromethyl)benzoyl]-amino}methyl)phenoxy]acetic acid;

2-hydroxy-5-[4-{[(4-pentylbenzyl)amino]carbonyl}benzyl)(3-phenyipropanoyl)-amino]benzoic acid;

4[(3-cyclopentylpropanoyl)(4-{[(4-pentylbenzyl)amino]carbonyl}benzyl)amino]-2-hydroxybenzoic acid;

2-hydroxy-4-{(4-{[(4-pentylbenzyl)amino]carbonyl}benzyl)[4-(trifluoromethyl)-benzoyl]amino}benzoic acid;

2-hydroxy-5-[{[2-(4-{[(4-pentylbenzyl)amino]carbonyl}phenyl)-1,3-thiazol-4-yl]methyl}(phenoxyacetyl)amino]benzoic acid;

2-hydroxy-5-{{[2-(4-{[(4-pentylbenzyl)amino]carbonyl}phenyl)-1,3-thiazol-4yl]methyl}[4-(trifluoromethyl)benzoyl]amino}benzoic acid;

5-([(6-chloropyridin-3-yl)carbonyl]{[2-(4-{[(4-pentylbenzyl)amino]carbonyl}-phenyl)-1,3-thiazol-4-yl]methyl}amino)-2-hydroxybenzoic acid;

5-((4-cyanobenzoyl){[2-(4-{[(4-pentylbenzyl)amino]carbonyl})phenyl)-1,3-thiazol-4-yl]methyl}amino)-2-hydroxybenzoic acid;

2-hydroxy-5-((3-methylbut-2-enoyl){[2-(4-{[(4-pentylbenzyl)amino]carbonyl}-phenyl) -1,3-thiazol-4-yl]methyl}amino)benzoic acid;

5-((3-cyclopentylpropanoyl){[2-(4-{[(4-phenoxybenzyl)amino]carbonyl}phenyl)-1,3-thiazol-4-yl]methyl}amino)-2-hydroxybenzoic acid;

2hydroxy-5-{{[2-(4{[(4phenoxybenzyl)amino]carbonyl}phenyl)-1,3-thiazol-4yl]methyl}[4(trifluoromethyl)benzoyl]amino}benzoic acid;

2-hydroxy-5-[{[2-(4-{[(4-phenoxybcnzyl)amino]carbonyl}phenyl) 1,3-thiazol-4-yl]methyl}(3-phenylpropanoyl)amino]benzoic acid;

5-(benzoyl{[2-(4-{[(4-phenoxybenzyl)amino]carbonyl}phenyl)-1,3-thiazol-4-yl]methyl}amino)-2-hydroxybenzoic acid;

[4-({{[2-(4-{[(4-pentylbenzyl)amino]carbonyl}phenyl)-1,3-thiazol-4-yl]methyl}[4-(trifluoromethyl) benzoyl]amino}methyl)phenoxy]acetic acid;

(4-{[{[2-(4-{[(4-pentylbenzyl)amino]carbonyl}phenyl)1,3-thiazol-4-yl]methyl}(3-phenylpropanoyl) amino]methyl}phenoxy)acetic acid;

[4-({{[2-(4-{[(4-phenylbutyl)amino]carbonyl}phenyl)1,3-thiazol-4-yl]methyl}[(trifluoromethyl)benzoyl]amino}methyl)phenoxy]acetic acid;

(4-{[{[2-(4-{[(4-phenylbutyl)amino]carbonyl}phenyl)1,3-thiazol-4-yl]methyl}[(3-phenylpropanoyl)amino]methyl}phenoxy)acetic acid;

[4-({{[2-(4-{[(4-phenylbutyl)amino]carbonyl}phenyl)1,3-thiazol-4-yl]methyl}[(2E)-3-phenylprop-2-enoyl]amino}methyl)phenoxy]acetic acid;

{4-[((N,N-dimethylglycyl){[2-(4-{[(4-phenylbutyl)amino]carbonyl}phenyl)-1,3-thiazol-4-yl]methyl}amino)methyl]phenoxy}acetic acid;

{4-[((cyclohexylcarbonyl){[2-(4-{[(4-phenylbutyl)amino]carbonyl}phenyl)-1,3-thiazol-4-yl]methyl}amino)methyl]phenoxy}acetic acid;

{4-[((phenoxyacetyl){[2-(4-{[(4-phenoxybenzyl)amino]carbonyl}phenyl)-1,3-thiazol-4-yl]methyl}amino)methyl]phenoxy}acetic acid;

[4-({{[2-(4-{[(4-phenoxybenzyl)amino]carbonyl}phenyl)-1,3-thiazol-4-yl]methyl}[4-(trifluoromethyl)benzoyl]amino}methyl)phenoxy]acetic acid;

(4-{[{[2-(4-{[(4-phenoxybenzyl)amino]carbonyl}phenyl)-1,3-thiazol-4-yl]methyl}(3-phenylpropanoyl)amino]methyl}phenoxy)acetic acid;

{4-[((cyclohexylcarbonyl){[2-(4-{[(4-phenoxybenzyl)amino]carbonyl}phenyl)1,3-thiazol-4-yl]methyl}amino)methyl]phenoxy}acetic acid;

[4-({[(2-{4-[(octylamino)carbonyl]phenyl}-1,3-thiazol-4-yl)methyl][4-(trifluoromethyl)benzoyl]amino}methyl)phenoxy]acetic acid; and (4-{[[(2-{4-[(octylamino)carbonyl]phenyl}-1,3-thiazol-4-yl)methyl](3-phenylpropanoyl)amino]methyl}phenoxy)acetic acid.

5. A pharmaceutical composition comprising at least one aryl dicarboxamide according to claim 3 and a pharmaceutically acceptable carrier, diluent, excipient, or combination thereof.

6. A pharmaceutical composition comprising at least one aryl dicarboxamide according to claim 2 and a pharmaceutically acceptable carrier, diluent, excipient, or combination thereof.

7. A method of preparing the aryi dicarboxainide of

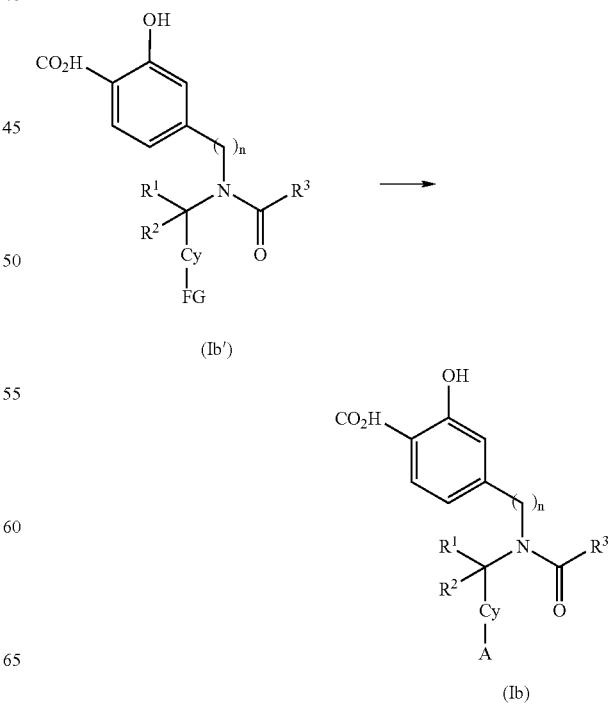

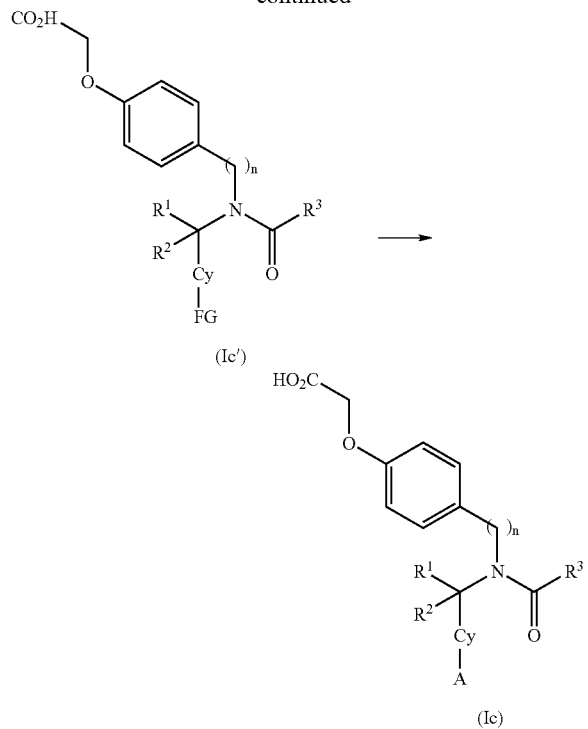

wherein FG is A or a leaving group,
wherein:
A is an aminocarbonyl moiety of the formula—CO—NHR⁶, wherein R⁶ is a phenyl group attached directly or through an alkylene group, a phenyl-phenoxy group, or an octyl group;
Cy is a phenyl group or a thiazole-phenyl group;
n is either 0 or 1;
$R^1$ and $R^2$ are hydrogen; and
$R^3$ is selected from the group consisting of: (:) an alkyl group optionally substituted with an amino group, and (ii) a cyclopentyl group, a cyclopentyl group, a phenyl group, or a pyridyl group, attached directly or through an alkylene group or an xox group, and optionally substituted with a cyano group or a fluoromethyl group.

8. A method of treating type II diabetes or obesity, comprising administering to a subject in need of such treatment an effective amount of at least one member selected from the group consisting of:

5-[(3-cyclopentylpropanoyl)(4-{[(4-phenoxybenzyl)amino]carbonyl}benzyl)amino[-2-hydroxybenzoic acid;

5-[(3-cyclopentylpropanoyl)(4-{[(4-phenoxybenzyl)amino]caxbonyl}benzyl)amino]-2-hydroxybenzoic acid;

[4-({{[2-{[4-{[(4-pentylbenzyl)amino]carbonyl}phenyl)-1,3-thiazol-4yl]methyl}-[(2E)-3-phenylprop-2-enoyl]amino}methyl)phenoxy]acetic acid;

5-[(3-cyclopentylpropanoyl)(4-{[(4-pentylbenzyl)amino]carbonyl}benzyl)amino]-2-hydroxybenzoic acid;

2-hydroxy-5-{(4-{[(4-pentylbenzyl)amino]carbonyl}benzyl)[4-(trifluoromethy)-benzoyl]amino}benzoic acid;

2-hydroxy-5-[[(4-{[(4-phenoxybenzyl)amino]carbonyl}-1,3-thiazol -2-yl) methyl](3-phenylpropanoyl)amino]benzoic acid;

5-{benzoyl[(4-{[(4-phenoxybenzyl)amino]carbonyl}-1,3,thiazol-2-yl)mathyl]-amino}-2-hydroxybenzoic acid;

2-hydroxy-5-{[(4-{[(4-phenoxybenzyl)amino]carbonyl}-1,3-thiazol-2-yl)methyl][4-(trifluoromethyl)benzoyl]amino}benzoic acid;

5-[(cyclohexylcaxbonyl)(4-{[(4-phenoxybenzyl)amino]caxbonyl}benzyl)amino]-2-hydroxybenzoic acid;

2-hydroxy-5-[(4-{[(4-phenoxybenzyl)amino]carbonyl}benzyl)(3-phenylpropanoyl)-amino]benzoic acid;

5-[benzoyl(4-}[(4-phenoxybenzyl)amino]carbonyl}benzyl)aminol]-2-hydroxybenzoic acid:

5-[acetyl(4-{[4-phenoxybenzyl)amino]carbonyl}benzyl)amino]-2-hydroxybenzoic acid;

5-[(4-cyanobenzoyl(4-{[(4-phenoxybenzyl)amino]carbonyl}benzyl)amino]-2-hydroxybenzoic acid;

2-hydroxy-5-[(phenoxyacetyl)(4-}[(4-phenoxybenzyl)amino]carbonyl}benzyl)-amino]-benzoic acid;

2-hydroxy-5-{(4-{[(4-phenoxybenzyl)amino]carbonyl}benzyl)[4-(trifluoromethyl)-benzoyl]amino}benzoic acid;

2-hydroxy-5-{(4-{[(4-phenoxybenzyl)amino]carbonyl}benzyl)[(2E)-3-phenylprop-2-enoyl]amino}benzoic acid;

5-(N,N-dimethylglycyl)(4-{[(4-phenoxybenzyl)amino]carbonyl}benzyl)amino]-2-hydroxybenzoic acid;

2-hydroxy-5-[(3-methylbut-2-enoyl)(4-{[(4-phenoxybenzyl)amino]carbonyl}benzyl-amino]benzoic acid;

2-hydxoxy-5-{[{4-[(octylamino)carbonyl]benzyl}(phenoxyacetyl)amino]methyl}-benzoic acid;

2-hydroxy-5-({{4-[(octylamino)carbonyl]benzyl}[4-(trifluoromethyl) benzoyl[-amino}methyl)benzoic acid;

2-hydroxy-5-({{(4-[(octyhamino)carbonyl]benzyl}[(2E)-3-phenylprop-2-enoyl]-amino}methyl)benzoic acid;

5-{[(3-cyclopentylpropanoyl)(4-{[(4-pentylbenzyl)amino]carbonyl}benzyl)-amino]methyl}-2-hydroxybenzoic acid;

2-hydxoxy-5-{[(4-{[(4-pentylbenzyl)amino]carbonyl}benzyl)(phenoxyacetyl)-amino]methyl}benzoic acid:

2-hydroxy-5-({(4-{[(4-pentylbenzyl)amino]caxbonyl}benzyl)[4trifluorometliyl)-benzoyl]amino}methyl)benzoic acid;

2-hydroxy-5-{[(3-methylbut-2-enoyl)(4-{[(4-pentylbenzyl)amino]carbonyl}-benzyl)amino]methyl}benzoic acid;

5-{[(3-cyclopentylpropanoyl)(4-{[(4-phenylbutyl)amino]carbonyl}benzyl)-amino]methyl}-2-hydxoxybenzoic add;

5{[(3-cyclopentylpropanoyl)(4-{[(4-phenylbutyl)amino]carbonyl}benzyl)-amino]methyl}-2hydroxybenzoic acid;

2-hydroxy-5-({[(4-{[(4pentylbenzyl)amino]carbonyl}-1,3-thiazol-2-yl)methyl][(2E)-3-phenylprop-2-enoyl]amino}methyl)benzoic acid;

[4-({(4-{[(4-phenoxybenzyl)amino]carbonyl}benzyl)[4-(trifluoromethyl)benzoyl]-amino}methyl)phenoxy]acetic acid;

2-hydroxy-5-[(4-{[(4-pentylbenzyl)amino]carbonyl}benzyl)(3-phenylpropanoyl)-amino]benzoic acid;

4-[(3-cyclopentylpropanoyl)(4-{[(4-pentylbenzyl)amino]carbonyl}benzyl)amino]-2-hydroxybenzoic acid;

2-hydroxy-4-{(4-{[(4-pentylbenzyl)amino]carbonyl}benzyl)[4-(trifluoromethyl)-benzoyl]amino}benzoic add;

2-hydroxy-5-[{[2-(4-{[(4-pentylbenzyl)amino]carbonyl}phenyl)-1,3-thiazol-4-yl](phenoxyacetyl)amino]benzoic acid;

2-hydxoxy-5-{{[2(4-{[(4-pentylbenzyl)amino]carbonyl}phenyl)-1,3-thiazol-4-yl]-(trifluorornethyl)benzayl]amino}benzoic acid;

5-([[(6-chloropyridin-3-yl)caxbonyl]{[2-(4-{[(4-pentyl-benzyl)amino]carbonyl}-phenyl)    -1,3-thiazol-4-yl]methyl}amino)-2-hydroxybenzoic add;

5-((4-cyanobenzoyl){[2-(4-{[(4-pentylbenzyl)amino]carbonyl}phenyl)-1,3-thiazol-4-yl]methyl}amino)-2-hydroxybenzoic acid;

2-hydroxy-5-((3-methylbut-2-enoyl){[2-(4{[(4-pentyl-benzyl)amino]carbonyl}-phenyl) -thiazol-4-yl]methyl)amino)benzoic acid;

5-((3-cyclopentylpropanoyl){[2-(4-{[(4-phenoxybenzyl)amino]carbonyl}phenyl)-1,3-thiazol    -yl]methyl)amino)-2-hydroxybenzoic acid;

2-hydroxy-5-{{2-(4-{[(4-phenoxybenzyl)aminocarbonyl)phenyl)-1,3-thiazol-4-yl]methyl}[4-(trifluoromethyl)benzoyl]amino}benzoic acid;

2-hydroxy-5-[{[2-(4-{[(4-phenoxybenzyl)amino]carbonyl}phenyl)-1,3-thiazol-4-yl]methyl}(3-phenyl-propanoyl)amino]benzoic acid;

5-benzoyl{[2-(4-{[(4-phenoxybenzyl)amino]carbonyl)phenyl)-1,3-thiazol-4-yl]methyl}amino}-2-hydroxybenzoic acid;

4-({{[2-(4-{[(4-pentylbenzyl)amino]carbonyl}phenyl)-1,3-thiazol-4-yl]methyl}[4-(trifluoromethy)benzoyl]amino}methyl)phenoxy]acetic acid;

(4-{[{[2-(4-{[(4-pentylbenzyl)amino]carbonyl}phenyl)-1,3-thiazol-4-yl]methyl}(phenylpropanoyl)amino]methyl)phenoxy)acetic acid;

[4-({{[2-(4-{[(4-phenylbutyl)amino]carbonyl}phenyl)-1,3-thiazol-4-yl]methyl}[4-(trifluoromethyl)benzoyl]amino)methyl)phenoxy]acetic acid;

(4-{[{[2-(4-{[(4-phenylbutyl)amino]carbonyl}phenyl)-1,3-thiazol-4-yl]methyl}(3-phenylpropanol)amino]methyl}phenoxy)acetic acid;

4-({{[2-(4-{[(4-phenylbutyl)amino]carbonyl}phenyl)-1,3-thiazol-4-yl]methyl}[(2E)-3-phenylprop-2-enoyl]amino)methyl}phenoxy]acetic acid;

{4-[((N,N-dimethylglycyl){[2-(4-{[(4-phenylbutyl)amino]carbonyl}phenyl)-1,3-thiazol-4-yl]methyl}amino)methyl]phenoxy}acetic acid;

{4-[((cyclohexylcarbyonyl){[2-(4-{[(4-phenylbutyl)amino]carbonyl}phenyl)-1,3-thiazol-4-yl]methyl)amino)methyl]phenoxy}acetic acid;

{4-[((phenoxyacetyl){[2-(4-{[(4-phenoxybenzyl)amino]carbonyl}phenyl)-1,3-thiazol-4-yl]methyl}amino)methyl]phenoxy}acetic acid;

[4-({{[2-(4-{[(4-phenoxybenzyl)amino]carbonyl}phenyl)-1,3-thiazol-4-yl]methyl}[4-(trifluoromethyl)benzoyl]amino}methyl)phenoxy]acetic acid;

(4-{[{[2-(4-{[4-phenoxybenzyl)amino]carbonyl}phenyl)-1,3-thiazol-4-yl ]methyl}(3-phenyl-propanoyl)amino]methyl)phenoxy)acetic acid;

{4-[((cyclohexylcarbonyl){[2-(4-{[(4-phenoxybenzyl)amino]carbonyl}phenyl)-1,3-thiazol-4-yl]methyl}amino)methyl}phenoxy}acetic acid;

[4-({[[(2-{4-[(octylamino)carbonyl]phenyl}-1,3-thiazol-4-yl]methyl][4-(trifluoromethyl)benzoyl]amino}methyl)phenoxy]acetic acid; and (4-{[[(2-{4-[(octylamino)carbonyl]phenyl}-1,3-thiazol-4-yl]methyl](3-phenylpropanoyl amino}methyl}phenoxy)acetic acid;

or a geometrical isomer thereof;

an optically active form thereof; or a pharmaceutically acceptable salt thereof.

* * * * *